(12) United States Patent
Sivertsen

(10) Patent No.: US 12,094,603 B2
(45) Date of Patent: Sep. 17, 2024

(54) ANALYZING AND RECORDING DEVICE QUALITY

(71) Applicant: Assaya LLC, Roswell, GA (US)

(72) Inventor: Clas Sivertsen, Lilburn, GA (US)

(73) Assignee: Assaya LLC, Roswell, GA (US)

( * ) Notice: Subject to any disclaimer, the term of this patent is extended or adjusted under 35 U.S.C. 154(b) by 546 days.

(21) Appl. No.: 17/346,045

(22) Filed: Jun. 11, 2021

(65) Prior Publication Data

US 2022/0399109 A1    Dec. 15, 2022

(51) Int. Cl.
 *G16H 40/63* (2018.01)
(52) U.S. Cl.
 CPC .................. *G16H 40/63* (2018.01)
(58) Field of Classification Search
 CPC ......... G16H 40/63; G16H 10/40; G16H 40/40
 See application file for complete search history.

(56) References Cited

U.S. PATENT DOCUMENTS

| 11,802,868 | B2 * | 10/2023 | Pulitzer | G01N 33/54388 |
| 2018/0164222 | A1 * | 6/2018 | Pulitzer | G06T 7/0012 |
| 2019/0096516 | A1 * | 3/2019 | Pulitzer | G01N 33/54388 |
| 2019/0122768 | A1 * | 4/2019 | Pulitzer | H04N 7/18 |

\* cited by examiner

*Primary Examiner* — Manuel A Rivera Vargas
(74) *Attorney, Agent, or Firm* — Nicholson De Vos Webster & Elliott LLP; Judith Szepesi

(57) ABSTRACT

A system including a processor and memory coupled to the processor. A communications interface is coupled to the processor for communicating with a central test database. A carrier is provided for receiving a cassette containing a lateral flow assay ("LFA") strip. An LFA strip reader is coupled to the processor for taking an image of the LFA strip and cassette and transmitting the image to the processor. The processor analyzes the image to determine a vendor of the cassette, analyzes the image of the LFA strip using a machine learning engine for quality defects in the LFA strip, generates an error when a quality defect is detected in the LFA strip, and reports the error to the central test database.

20 Claims, 23 Drawing Sheets

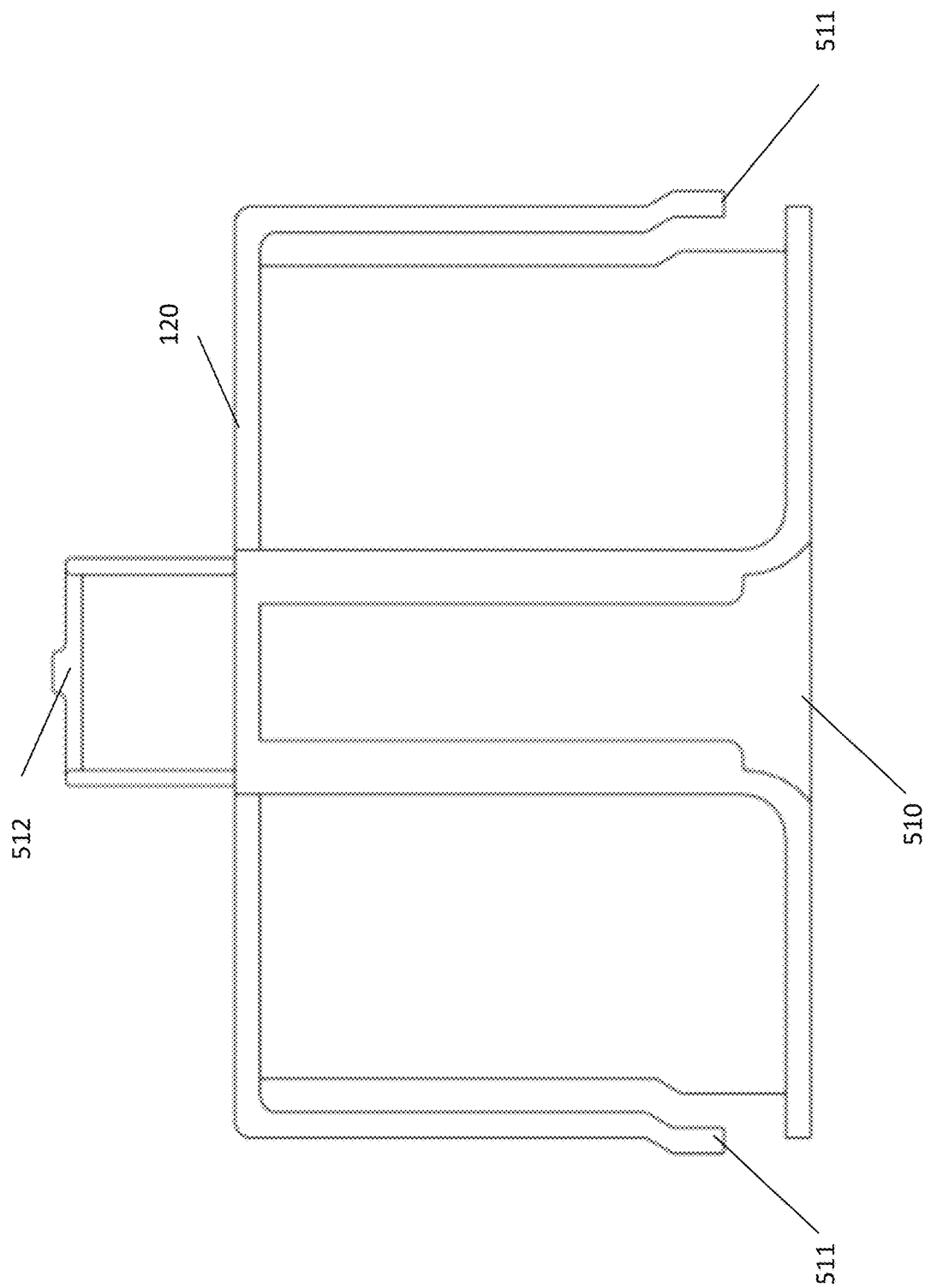

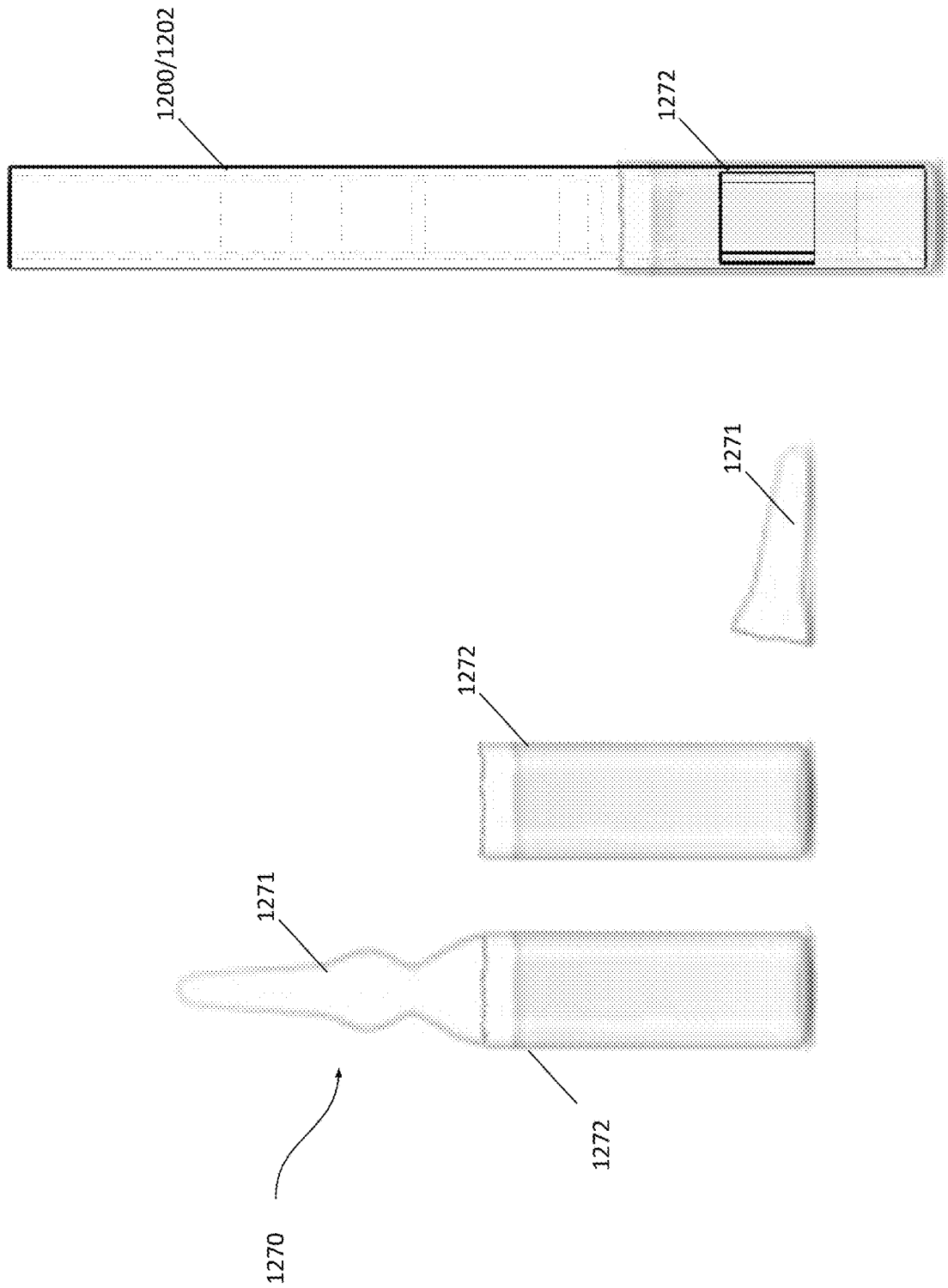

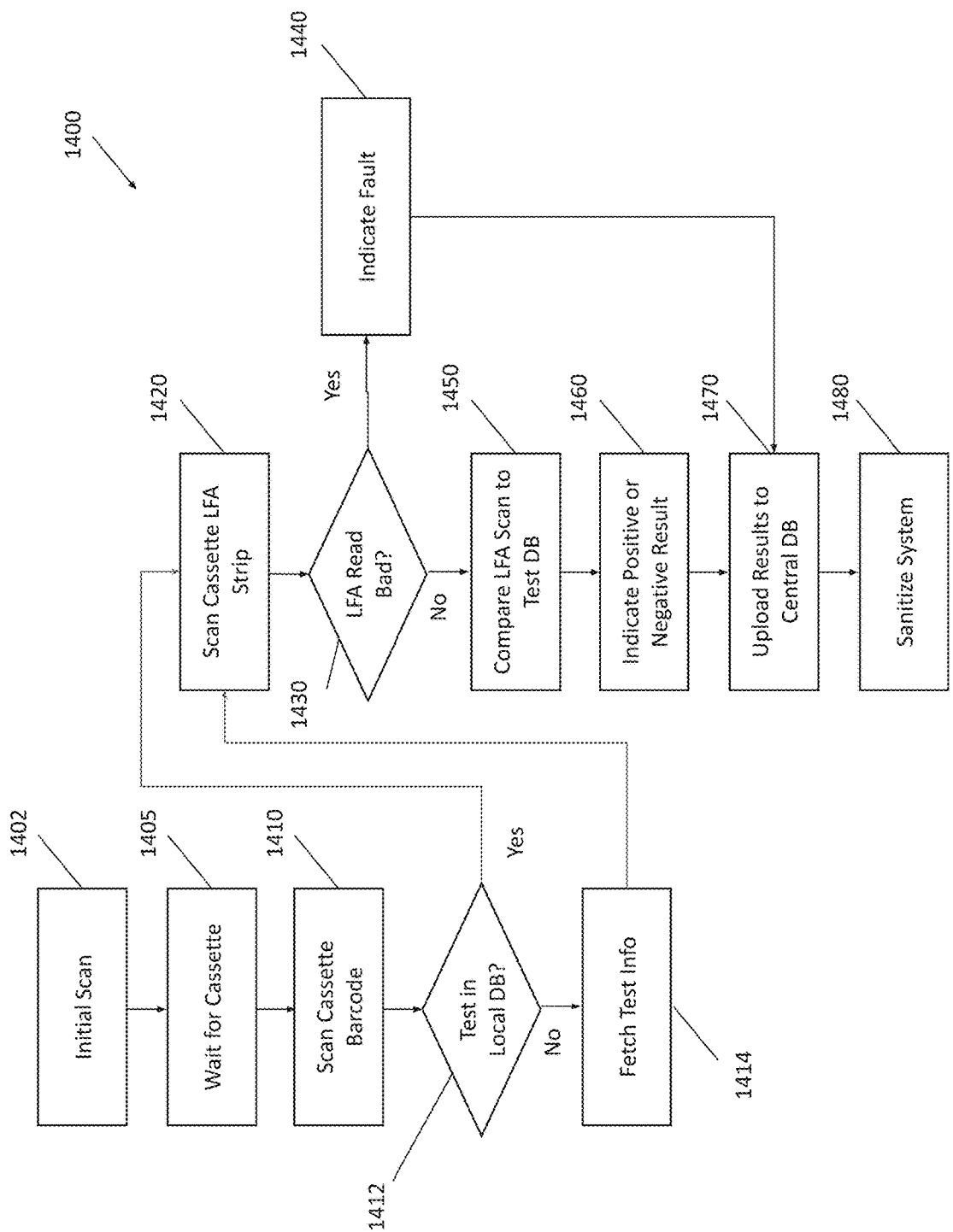

ANALYZING AND RECORDING DEVICE QUALITY

CROSS REFERENCE TO RELATED APPLICATIONS

This patent application is related to application, U.S. Ser. No. 17/079,513, titled "Medical Test Strip Analysis," filed concurrently with the present application on Oct. 25, 2020.

BACKGROUND

The present invention generally relates to quality measurement and more specifically, to a device quality analysis and recording system and method.

Coronavirus Disease 2019 ("COVID-19") is spreading throughout the country and the world caused by the spread of a novel coronavirus called SARS-CoV-2. With the rapid spread of the disease, testing quickly, accurately, and efficiently is becoming more important. Testing may be performed using a lateral flow assay ("LFA") strip present in an assay tube or cassette. The results of the test are determined by examining the LFA strip by looking for the presence of, for example, visual stripes on the LFA strip. Therefore, the quality of the LFA strip is important in order to get an accurate test result.

SUMMARY

Embodiments of the present invention are directed to a system having a processor and memory coupled to the processor is provided. A communications interface is coupled to the processor for communicating with a central test database. A carrier is provided for receiving a cassette containing a lateral flow assay ("LFA") strip. An LFA strip reader is coupled to the processor for taking an image of the LFA strip and cassette and transmitting the image to the processor. The processor analyzes the image to determine a vendor of the cassette, analyzes the image of the LFA strip using a machine learning engine for quality defects in the LFA strip, generates an error when a quality defect is detected in the LFA strip, and reports the error to the central test database.

Additional embodiments of the present invention are directed to a computer implemented method. The method receives a cassette containing a lateral flow assay ("LFA") strip and generates, using a processor, an image of the cassette and the LFA strip. The method analyzes, by the processor, the cassette and LFA strip for quality defects, generates, by the processor, an error when the analysis finds a quality defect, and sends, by the processor, the error and the image of the cassette and the LFA strip to a central test database when a quality defect is found.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 5 depicts a top-down view of a sample carrier used in the testing device according to an embodiment of the present invention;

FIG. 12b depicts a view of an assay tube and an ampule according to embodiments of the present invention;

Figure 1:
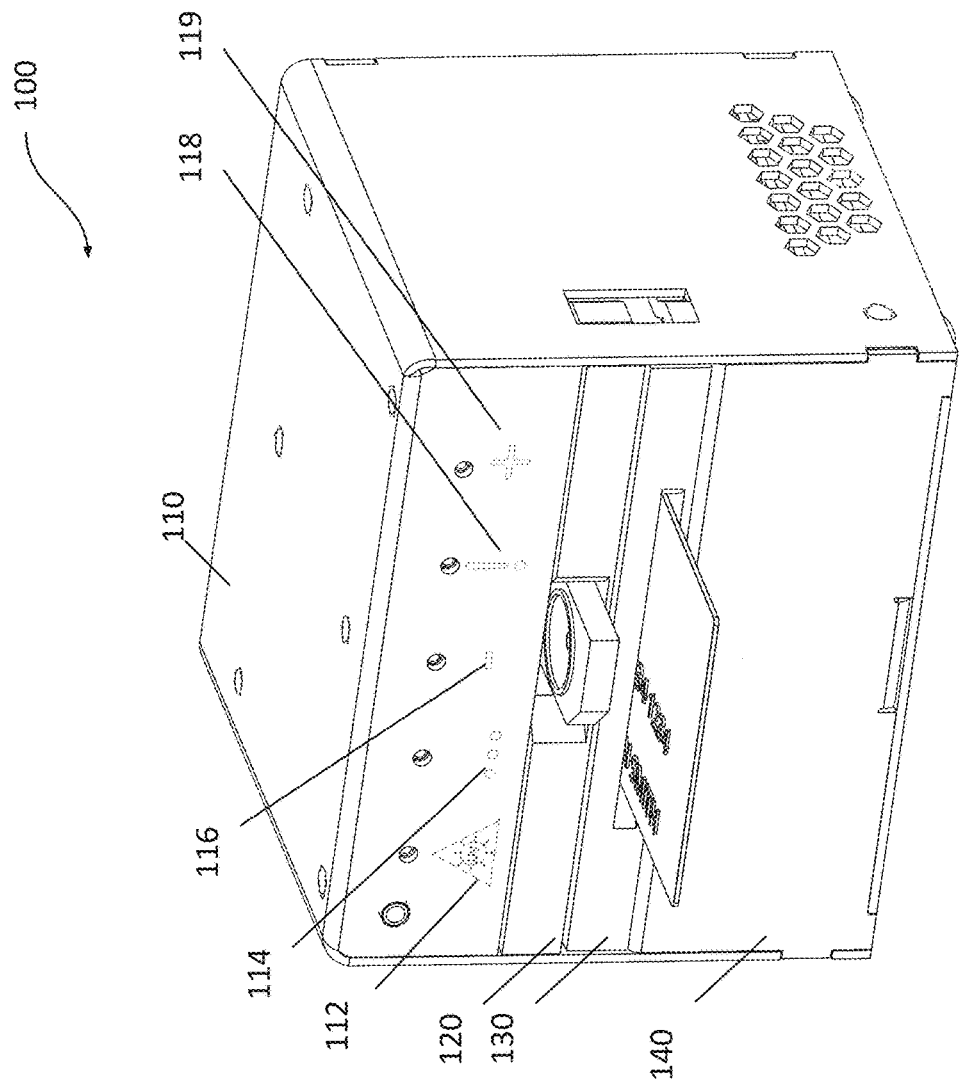
FIG. 1 depicts an orthogonal view of a testing device according to an embodiment of the present invention.

The diagrams depicted herein are illustrative. There can be many variations to the diagrams or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two- or three-digit reference numbers. With minor exceptions, the leftmost digit(s) of each reference number corresponds to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Turning now to an overview of technologies that are more specifically relevant to aspects of the invention, as previously stated, SARS-CoV-2 is spreading rapidly around the country and around the world resulting in a large portion of the population being at risk of developing COVID-19. It is imperative to test, often repeatedly, the population for SARS-CoV-2, and present testing systems are inadequate.

Present testing systems often require a nasal swab to get samples from a patient. This is very uncomfortable for the patient and requires a doctor, nurse, or technician to get very close to the patient, putting her at risk for developing COVID-19. Some tests exist that involve blood or saliva, but those tests, like the nasal tests, often take a great deal of time in order to get results back to the patient. By the time that test results are returned to the patient, the patient, if positive for SARS-CoV-2, may have infected dozens of others, thus spreading the illness.

A polymerase chain reaction ("PCR") test is currently the gold standard, as it is most sensitive. But because of the massive volumes of tests and due to the multitude of steps in collecting, storing, shipping, receiving, extracting, preparing, actually testing, collecting results, and distributing results, the actual result data have shown to be error prone due to the many possibilities of human error along the way. Because PCR tests are so sensitive there is also a high risk of cross contamination. Coupling that with the high increase in the volume of such tests and the shortage of skilled labor in laboratories, this further adds to the actual inaccuracy in the test data.

Furthermore, present testing systems do not clearly link a sample taken to a patient's identity. Samples must be labeled, and mistakes are easily made. Results of tests are not returned or stored in any type of database, either locally at the testing device or centrally. This requires difficult and error-prone data collection and entry. These time-consuming and error-riddled techniques are not up to the task of tackling a global pandemic.

Turning now to an overview of the aspects of the invention, one or more embodiments of the invention address the above-described shortcomings of the prior art by providing a testing system, known as an Integrated Strip Sampler™, that provides fast results and accurately ascribes those results to a patient's identity without requiring manual data entry, collection or labeling. Rapid antigen and antibody tests and associated reading methods become crucial in improving the speed and quality of test data. Because the invention described herein uses a computerized reader rather than relying on human interpretation, systems and method described herein are not only more accurate in differentiating a positive from a negative from an invalid test result, but they may also visually read and store the actual concentration of the pathogen so that analytics can be performed across a large number of patients, which can in turn be used by government, research institutes, vaccine developers, and pandemic planners implementing prevention measures to reduce the spread of future diseases. Lastly, the embodiments of the invention described herein substantially reduces the amount of materials, such as plastics which helps reduce the amount of waste in landfills and greatly reduces the amount of biological waste needing to be handled and safely disposed of.

The method uses a uniquely coded testing collection assay tube to collect saliva from a patient and read the resulting indication on the collection assay at a testing device. As the testing collection assay tube is uniquely coded, there is reduced risk that the test result is linked to the wrong patient. Even in the absence of a uniquely coded testing assay, for example when using the testing device with a non-coded testing cassette, the testing device receives an ID from the patient, such as a government issued ID, such as a passport, national ID card, or driver's license, to link the test result from the testing device with the patient.

Additionally, the testing device consistent with embodiments of the present invention includes interchangeable carriers that hold a variety of testing cassettes, in addition to the uniquely coded testing assay. Thus, the testing device is compatible with a wide-range of testing cassettes. As the testing device may be coupled to the Internet or a remote server, updates to the testing device may be made automatically or manually and remotely. There is no need to go into the field to update a testing device when new tests are present.

In addition, the testing device of the present invention includes a powerful computer that can store testing protocols for a full gauntlet of different tests. Tests are not limited to COVID-19 testing, but can include reading any type of test strip, or test carriage, for any type of disease, syndrome, virus, or bacteria. The results of any of these tests are uploaded to a central database for providing to the patient and for later use and analysis. Data collected in the central database may be anonymized for data mining purposes.

The testing device may also communicate with a web browser or dedicated app on a patient's mobile phone, tablet, or computer for providing the patient with test results and logging.

FIG. 1a depicts an orthogonal view of a testing device 100 according to an embodiment of the present invention. The testing device 100 is enclosed by a case 110. The case 110 includes a plurality of electronics for analyzing a lateral flow assay ("LFA") strip present in an assay tube or cassette. A removable carrier 120 has an opening in which the assay tube, cassette, or card is placed. During the remainder of this description, whenever the term "cassette" is used that term includes any of an assay tube, cassette, or card. The LFA strip provides indicators (stripes at various places along the LFA strip) that indicate the presence of analytes present in a sample. The testing device 100 includes an LFA strip reader having a plurality of LED's at a variety of wavelengths that shine upon the sample and a camera that images the sample, sending the image to a computer present in the testing device 100 for analysis. As a relatively powerful computer receives the image of the LFA strip, the computer can adjust for any misalignment of samples. In addition, in exemplary embodiments of the invention, one of the light sources can provide UVC light for sterilizing the testing device 100 prior to a new assay tube or cassette being placed in the testing device 100.

Since the assay tube used in conjunction with the present invention and to be discussed later has a unique barcode associated with it, the camera in the device not only reads the LFA strip, but also the barcode, providing both images to the computer in the testing device 100. When a barcode is not present, the camera provides a visual feature to the computer. Such a visual feature may be the shape of the inserted cassette, text on the cassette, presence or absence of one or more barcodes, data matrices or QR codes, or one or more colors present on the cassette, for example. The computer may then associate the unique ID with the test results and upload the results to a central database where it is provided back to the patient and/or caregiver.

As the testing device 100 may be a headless device (one lacking a keyboard or screen for input and a screen or printer for output), a plurality of indicators on an indication panel is present on the front of the testing device 100 for indicating, for example, disinfecting in process 112, testing-in-process 114, negative results 116, invalid 118, or positive results 119 from the sample.

Testing device 100 also includes a patient identification reader for reading patient identification information, such as card reader 130 for reading an identification card from a patient to associate the patient with the received assay tube or cassette. In an exemplary embodiment of the invention, the card reader may be a smart card reader to read a government issued ID, such as a passport, national ID car, or smart driver's license or it may read a credit card associated with the patient. Those skilled in the art will appreciate after reading this disclosure that other readers may also be used: for example, near field communication from a patient's device, such as her mobile phone, may be used to associate the patient with the sample or a magnetic strip may be read from a credit card lacking a smart chip. These variations are all contemplated to be used. In this way, when using the testing device 100 with cassettes that lack a unique identifier, the test result remains associated with the patient. No user input is needed beyond the identification card.

As stated previously, the testing device 100 may be in communication over, for example, Ethernet, WiFi, or mobile communications (such as 3G, 4G, and 5G, for example, to a central database. Test results are linked to the patient at the testing device 100 and provided to the central database following a test. The test results may then be further shared with the patient's healthcare provider and/or directly to the patient. A rich database of information is developed in the central patient database, and following anonymization, may be mined for demographic or other information relating to the test being taken.

Linking the testing device 100 to a central server also provides an additional benefit, as new tests are developed that use LFA strips, new profiles for tests may be downloaded, either automatically or pushed manually, from a central test database to the testing device 100. Thus, there is no need for expensive field technicians to update the testing device 100. Such updates happen automatically.

Figure 2:
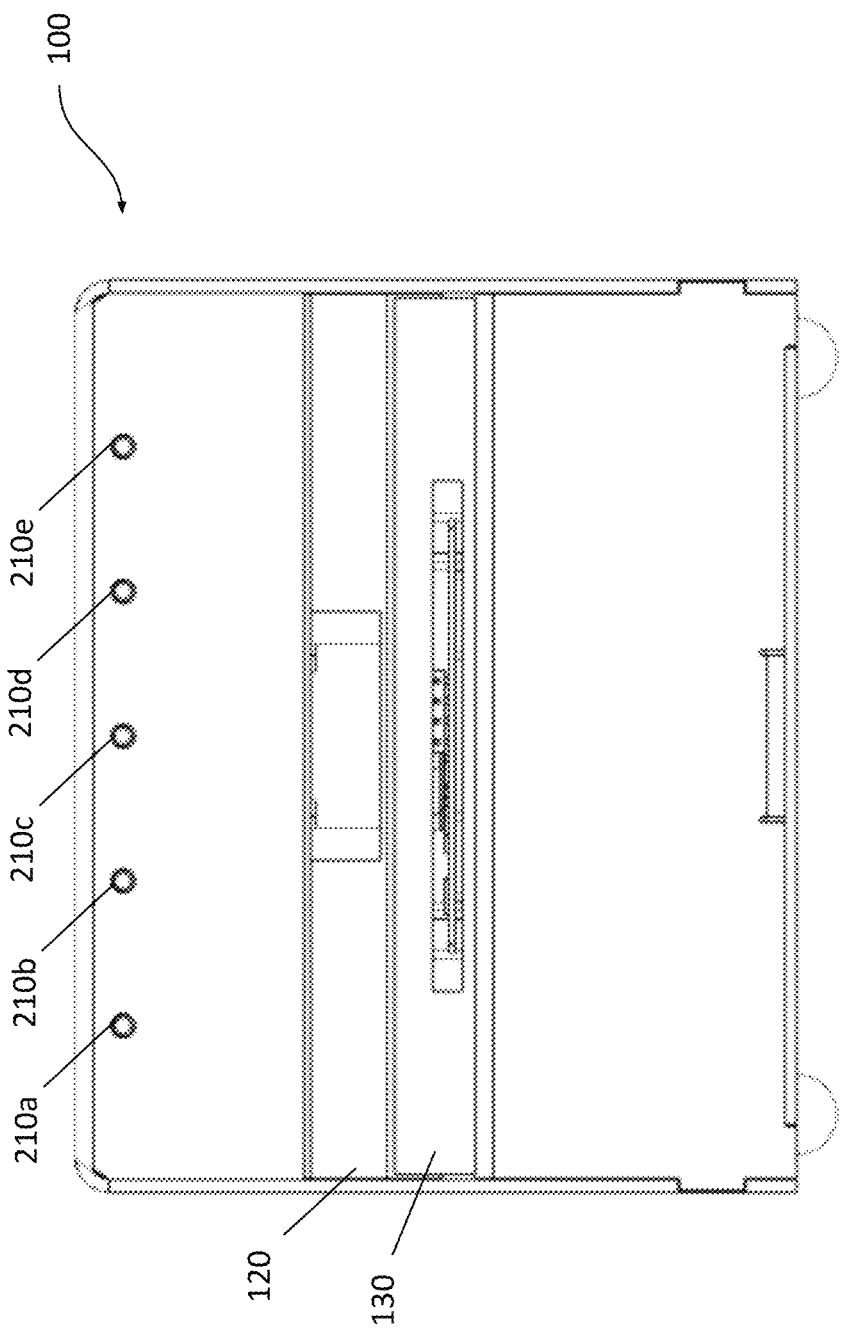
FIG. 2 depicts a front view of the testing device according to an embodiment of the present invention.

FIG. 2 depicts a front view of the testing device 100 according to an embodiment of the present invention. The front view again shows the removable carrier 120 for holding a cassette or assay tube and the card reader 130. In addition, five indicators, for example LED's, provide test results to a patient who is using the test device 100. In an exemplary embodiment, a sterilization indicator 210a that shows when sterilization activity is occurring within testing device 100, connectivity indicator 210b, positive result indicator 210c, fault indicator 210d, and negative result indicator 210e may be provided. An additional power indicator with a power button 440 may be included to power the testing device 100 on and off.

Figure 3:
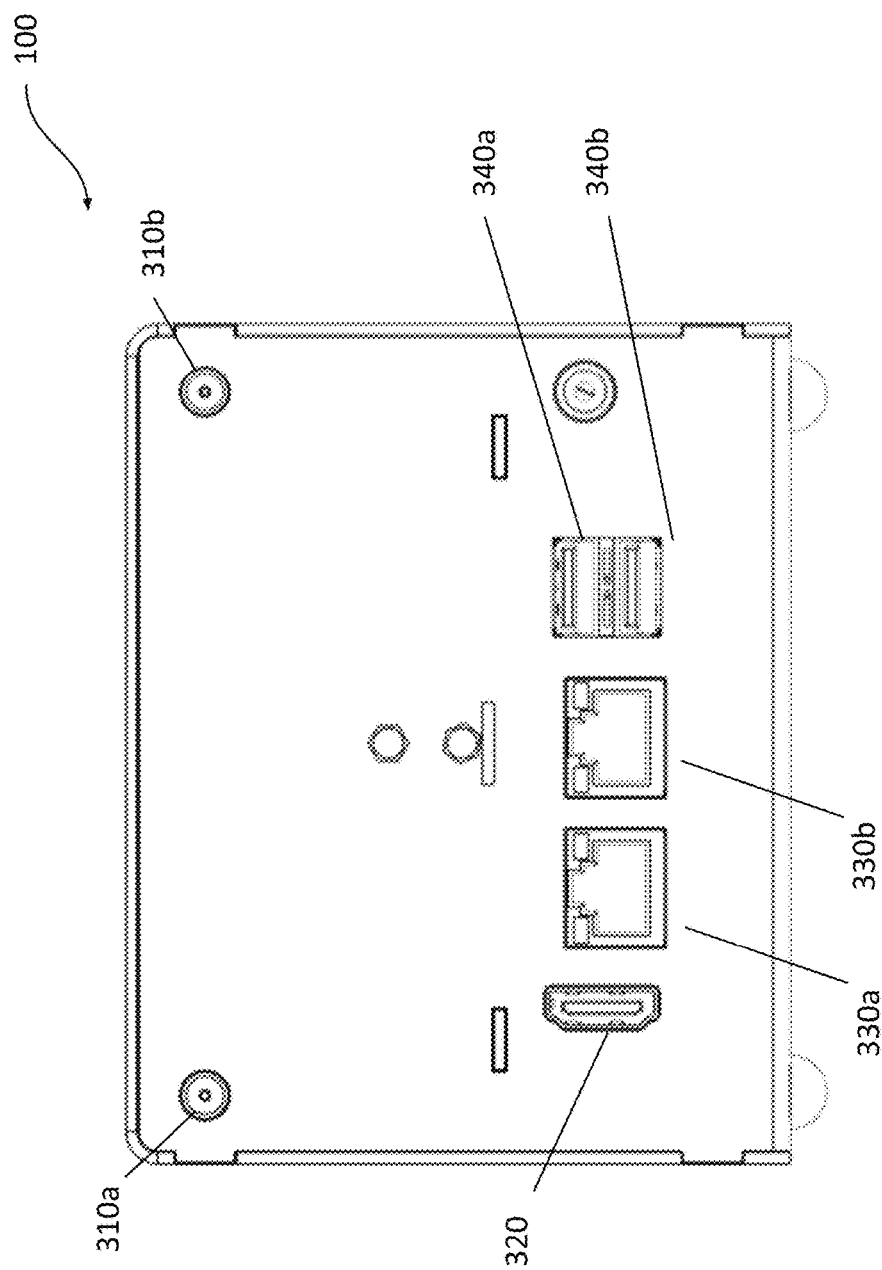
FIG. 3 depicts a back view of the testing device according to an embodiment of the present invention.

FIG. 3 depicts a back view of the testing device 100 according to an embodiment of the present invention. The back view of the testing device 100 shows various connectivity features present in an exemplary testing device 100. Testing device 100 may have a port for a display, such as HDMI port 320, Ethernet ports 330a and 330b, and USB ports 340a and 340b. Thus, while the testing device is primarily designed to be headless, if placed in a lab or a doctor's office the testing device also supports connection to a monitor and a keyboard. Results may then be shared with a healthcare professional on the display, and since the testing device 100 includes a full computer, it can support additional functions for the healthcare provider.

Figure 4A:
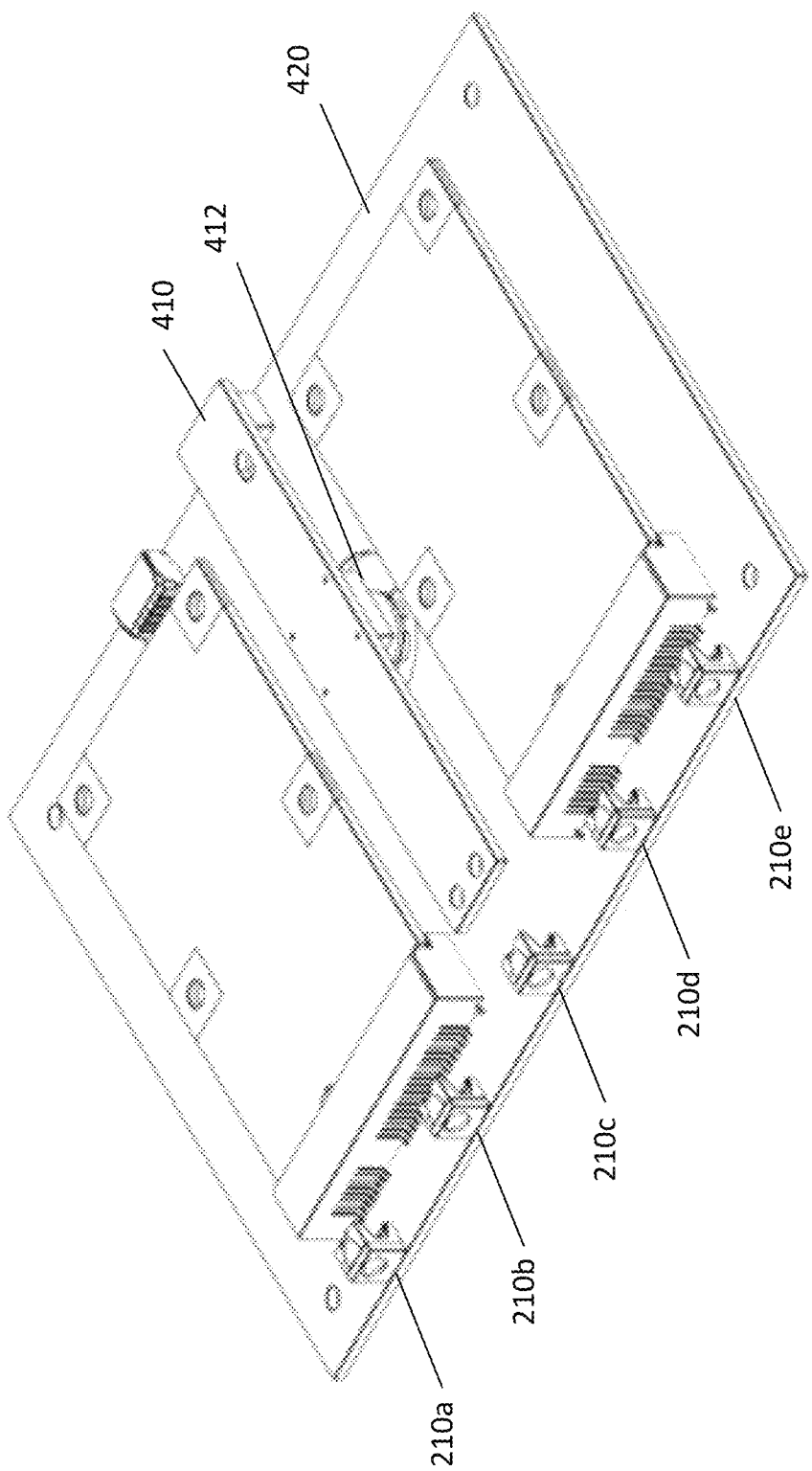
FIG. 4a depicts an orthogonal view of an LED testing and indicating board within the testing device according to an embodiment of the present invention.

FIG. 4a depicts an orthogonal view of an LED testing 410 board and indicating board 420 within the testing device 100 according to an embodiment of the present invention. The LED testing board 410 includes a plurality of LED's (not shown) to provide a variety of wavelengths of light that shine upon the LFA strip. The LED testing board 410 may include a UVC light source (not shown) to sterilize the portion of the testing device 100 that comes in contact with the sample. The LED testing board 410 includes a camera to take an image of a barcode present on an assay tube and of any LFA strips inserted into the testing device 100. These images are then communicated to the on-board computer within the testing device 100. The LED testing board 410 resides on the indicating board 420 that supports the indicators previously described. A hole in the indicating board 420 allows for the camera 412 on the LED testing board 410 to view the LFA strip. The LED testing board also contains a temperature and a humidity sensor.

Figure 4B:
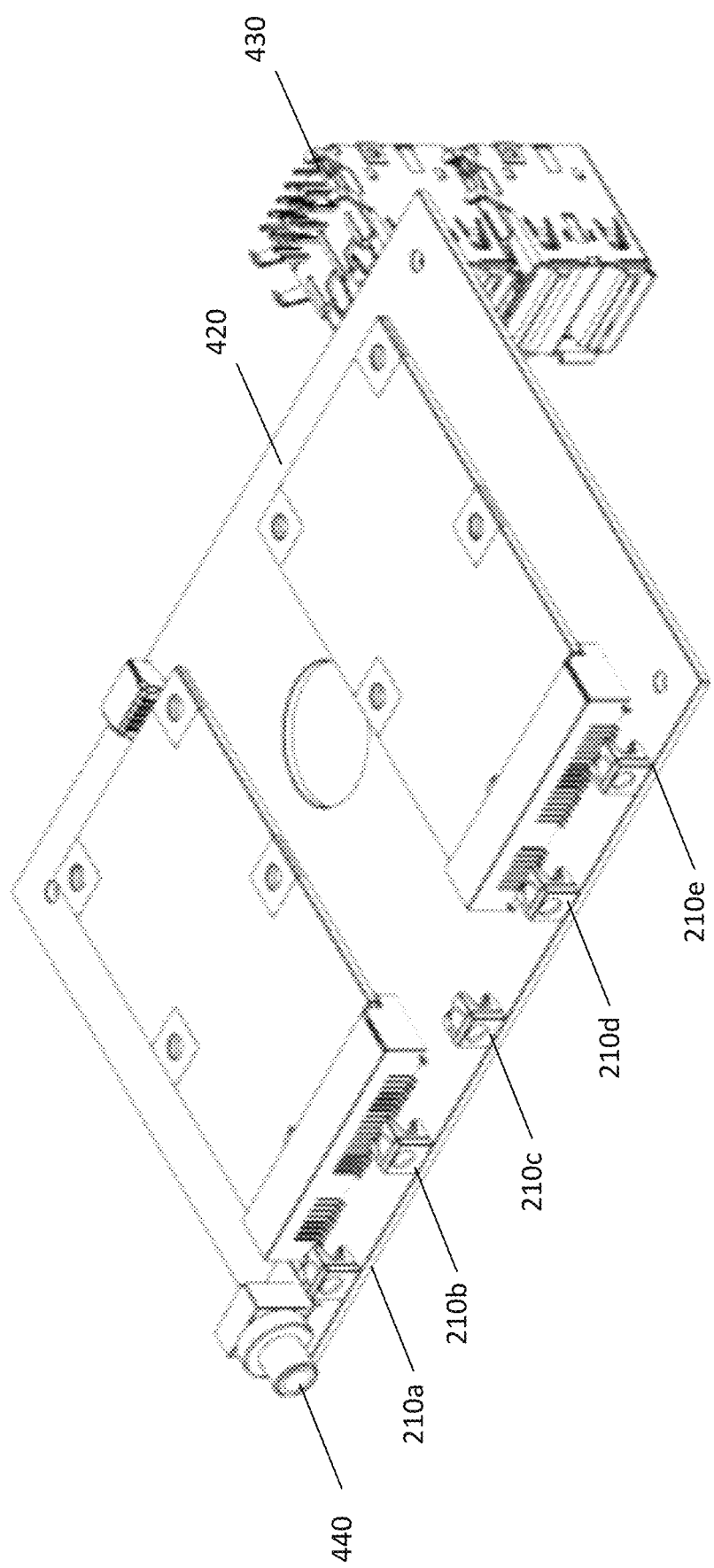
FIG. 4b depicts an orthogonal view of another embodiment of an indicating board within the testing device according to an embodiment of the present invention.

FIG. 4b depicts an orthogonal view of another exemplary embodiment of the indicating board 420 within the testing device 100 according to an embodiment of the present invention. A power switch 440 may be provided on the indicating board 420 to power the testing device 100 on and off. A mult-port USB connector 430 may be provided that allows for a carrier, such as sample carrier 120 to have electronic features that communicate with a host PC and its software. The positioning of the USB connectors relative to the sample carriers are aligned such that a PCB mounted within the sample carrier can use edge gold fingers in the same position as a typical USB connector, thus eliminating the need for an actual USB connector to be mounted on the PCB, and the USB connection between the PCB and the USB connector 430 is made when the sample carrier is inserted.

FIG. 5 depicts a top-down view of a sample carrier 120 used in the testing device according to an embodiment of the present invention. The sample carrier 120 receives an assay tube or carriage containing an LFA strip in opening 510 and supports it while camera 412 takes an image of the LFA strip. It is removable in an exemplary embodiment, so that as testing carriages or assay tubes change in the future, it may be swapped out. The sample carrier may include an active USB controller coupled to a mechanical switch or photo-optical device for sensing the presence of the assay tube or carriage. There are features on the sides 511 to latch with the chassis as the sample carrier is installed in the chassis, and a structure that serves like a spring 512 in the rear both holding the carrier in place during shipping and providing tension.

Figure 6A:
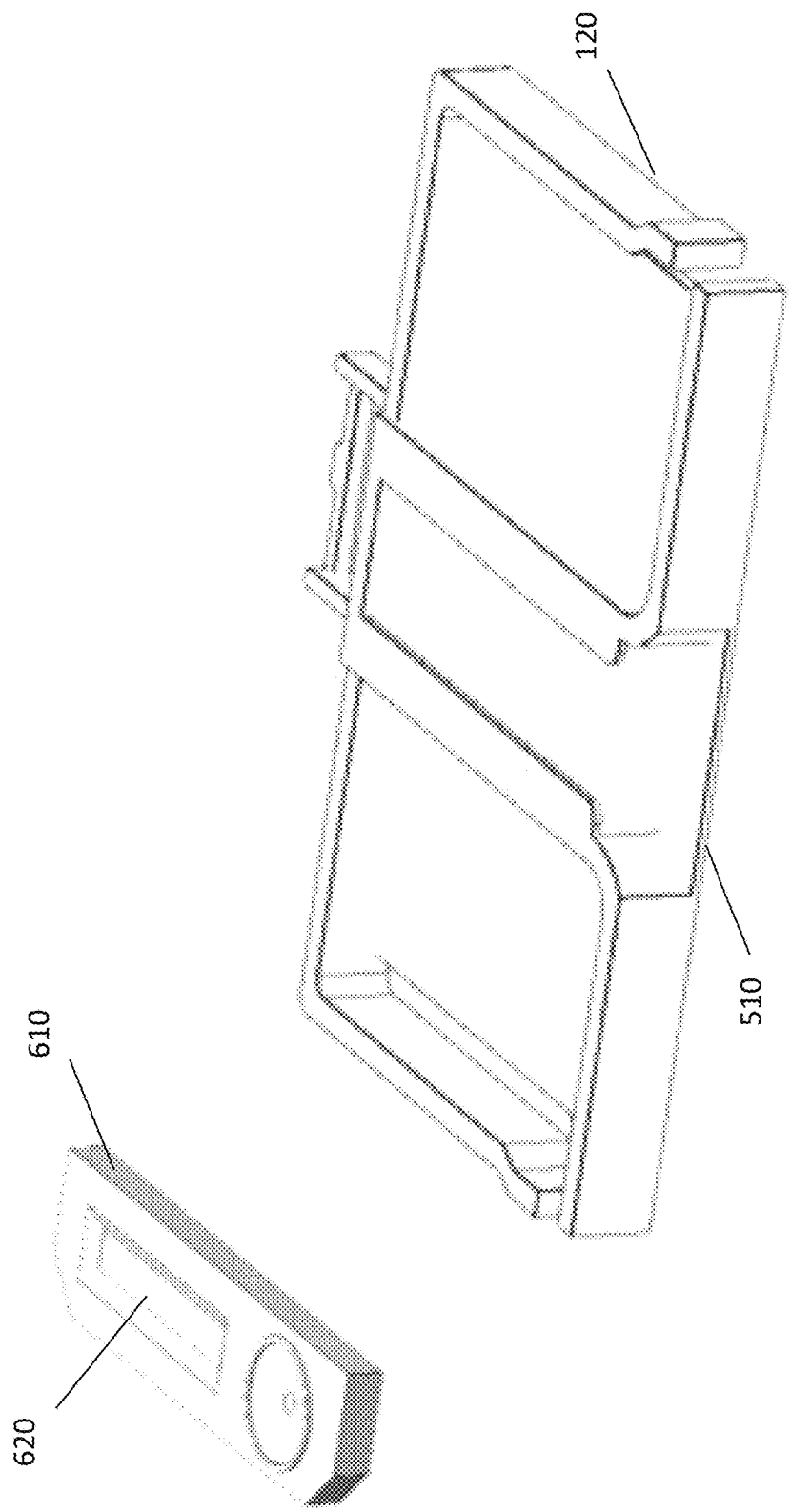
FIG. 6a depicts an orthogonal view of the sample carrier with a sample cassette used in the testing device according to an embodiment of the present invention.
Figure 6B:
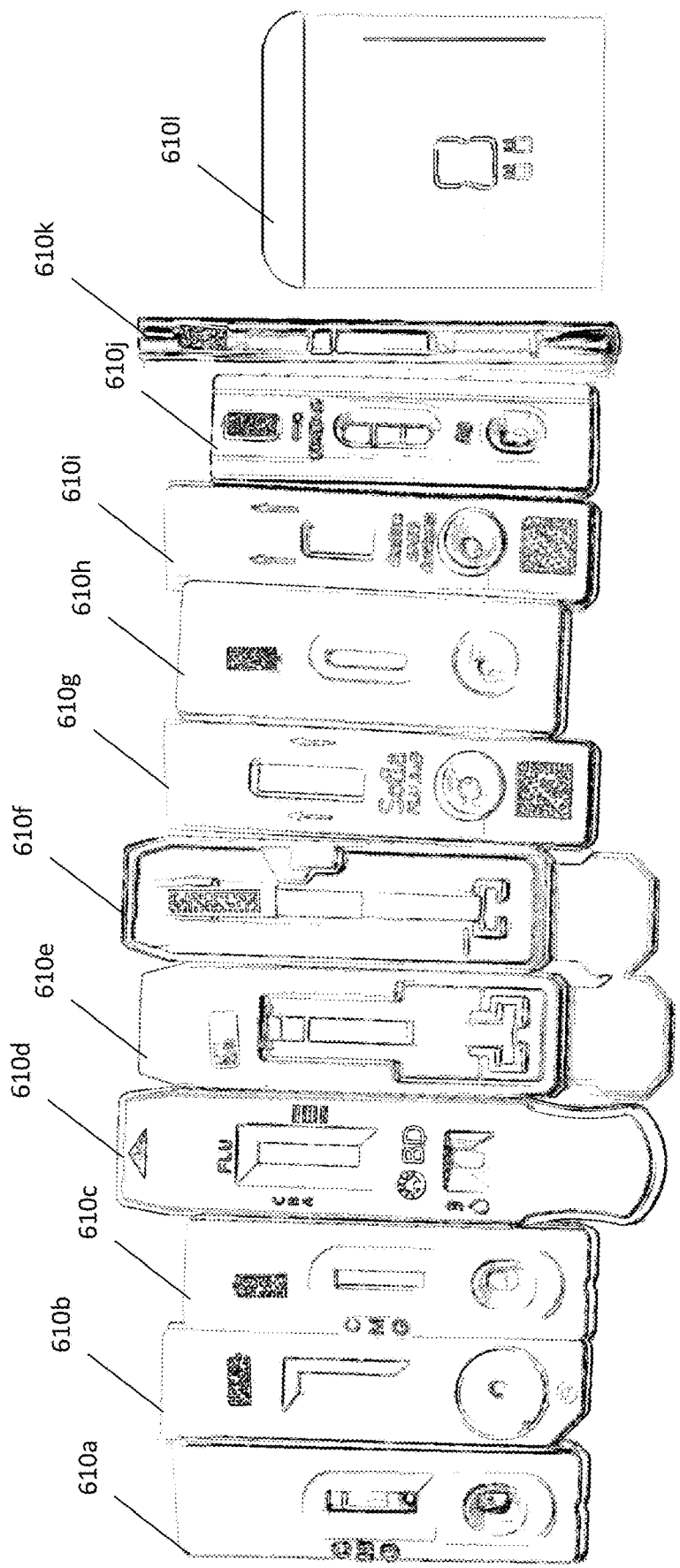
FIG. 6b depicts a plurality of cassettes that may be used in conjunction with the testing device according to an embodiment of the present invention.

FIG. 6a depicts an orthogonal view of the sample carrier 120 with a sample cassette 610 containing an LFA strip 620 used in the testing device 100 according to an embodiment of the present invention. FIG. 6b depicts a plurality of cassettes 610a-1 that may be used in conjunction with the testing device 100. Cassette 610k is a clear assay and cassette 610l is a card containing an LFA test strip.

Figure 6C:
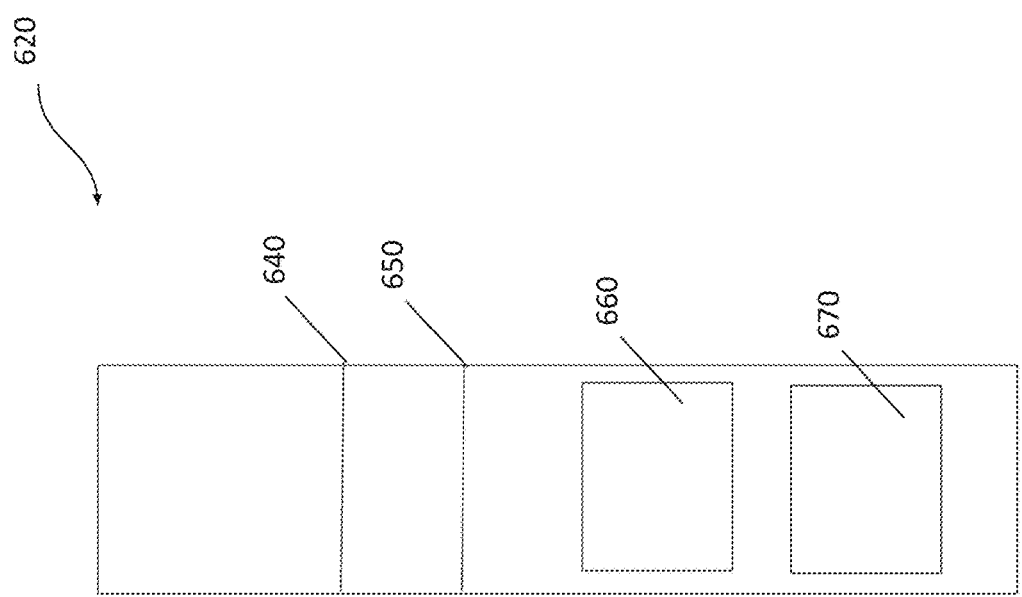
FIG. 6c depicts a lateral flow assay strip within the cassette according to an embodiment of the present invention.

FIG. 6c depicts the LFA strip 620 within the cassette 610 according to an embodiment of the present invention. The LFA strip 620 has at least one control line 640, test line 650, conjugate pad 660, and analyte pad 670. An analyte containing a sample from a domain is placed on the analyte pad 670. The analyte flows up the LFA strip 620 through the area of the strip having the conjugate pad 660, test line 650, and control line 640. Testing systems may be used in multiple domains. The domain, mentioned above, is the human domain, but testing is also performed in other domains, such as animals and the environment, for example. Reference to a domain herein is reference to any situation, for example, human testing, animal testing, environmental testing, and food testing.

The material of the test line 650 provides a positive result in the presence of a chemical-of-interest being tested for in the domain and a negative result in the absence of the chemical-of-interest being tested for in the domain. Where the chemical-of-interest can be a pathogen, or a piece of a pathogen, a biological marker, such as a protein of a chemical organic or inorganic, and where the biological marker can specifically be a substance such as the active ingredient in a drug, food additive, or environmental pollutant.

Figure 7A:
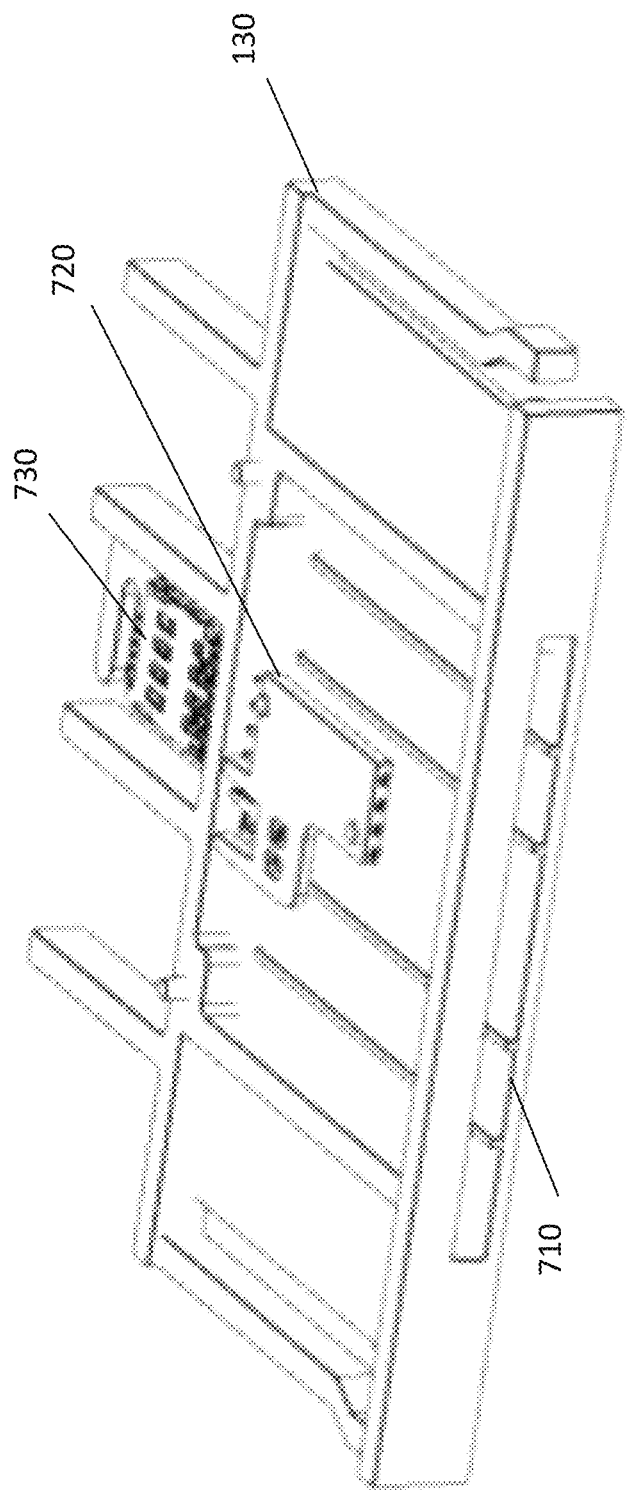
FIG. 7a depicts an orthogonal view of a card reader used in the testing device according to an embodiment of the present invention.
Figure 7B:
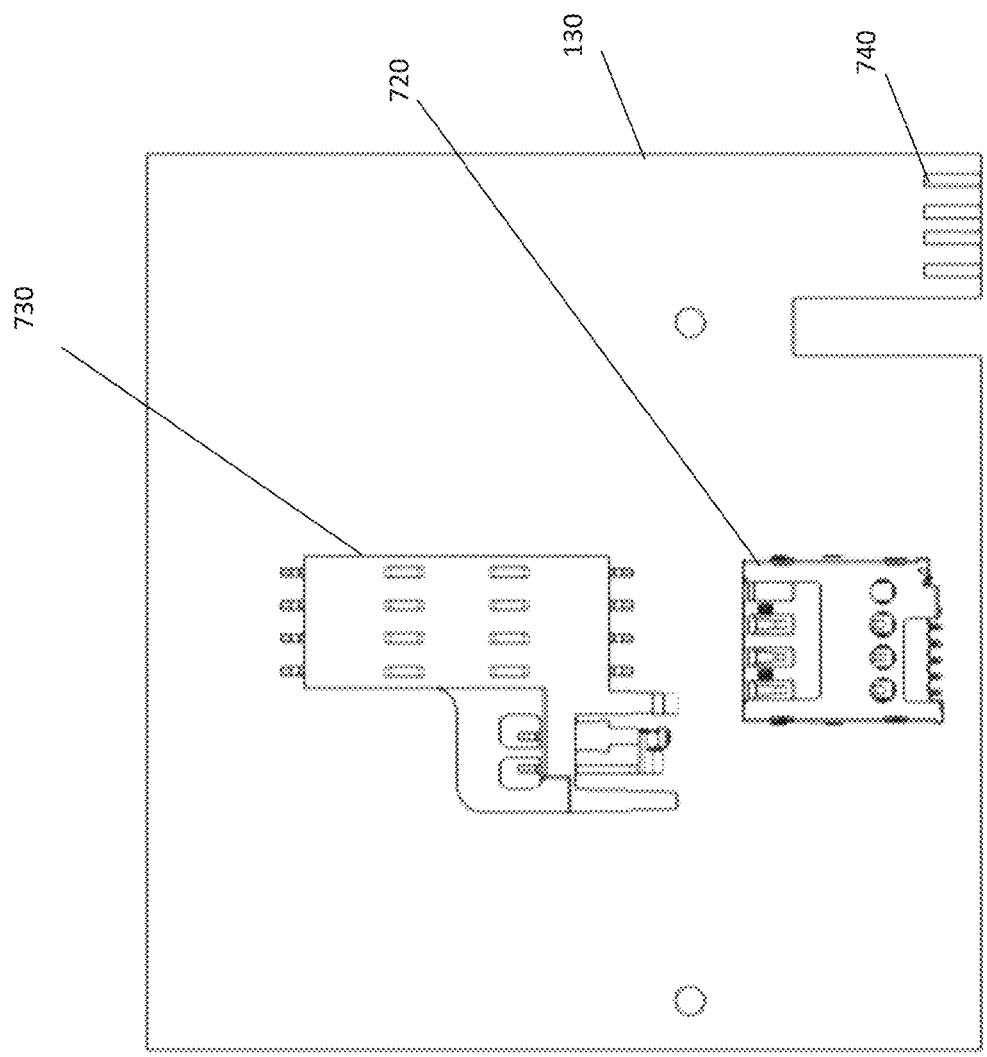
FIG. 7b depicts a top view of the card reader used in the testing device according to an embodiment of the present invention.

FIG. 7 depicts an orthogonal view of a removable card reader 130 used in the testing device 100 according to an embodiment of the present invention. As previously discussed, the card reader 130 receives a smart card, such as a credit card or national ID card, reads it with smart reader 720 and provides the read information to the computer within the testing device 100. In alternative embodiments, the removable card reader 130 can read magnetic strips on credit cards or be modified for near field communication to read identifying information from a patient's mobile phone or tablet. Removable card reader 130 may have a secondary smart card reader 740 for inserting a smart card from a health care provider, such as a medical professional. For example in Taiwan doctors offices have smart card readers where patients can insert their cards, but the reader also requires a second smart card to be inserted by the doctor with their credentials for added security. The health care provider's smart card would be inserted into a second card or smart card slot 730 before the removable card reader 130 is inserted into the testing device 100.

The removable card reader 130 may have gold fingers to permit the removable card reader 130 to be plugged into the USB connector 340, without having to physically mate a printed circuit board in the removable card reader 130 with a computer 800 (discussed with respect to FIG. 8 below). The removable card reader 130 may also be configured to receive the smart card upside down. This configuration would place the smart card reader 740 facing up on a floor of the removable card reader 130 and include a camera above the removable card reader 130 to read and communicate a signature from the smart card to the computer 800.

In an alternative embodiment of the invention, instead of a card reader being separated from the sample carrier, the card reader and sample carrier are in the same reception tray, such that an identification card (such as a driver's license) and assay tube or carriage are inserted side-by-side. In this embodiment, two cameras above the reception tray may be used, where a first camera reads the assay tube or carriage and a second camera reads the identification card visually, such as by PDF-417. PDF417 is a stacked linear barcode format used in a variety of applications such as transport, identification cards, and inventory management. "PDF" stands for Portable Data File. The "417" signifies that each pattern in the code consists of 4 bars and spaces in a pattern that is 17 units (modules) long.

Figure 8:
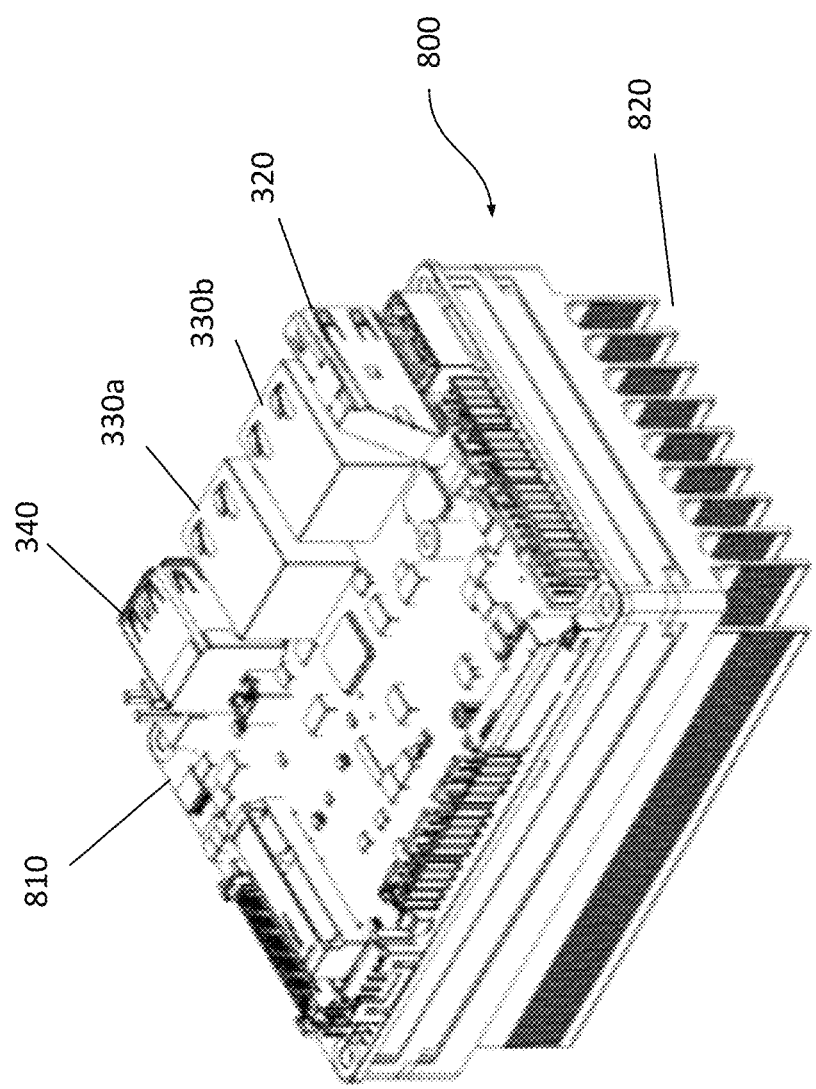
FIG. 8 depicts an orthogonal view of a computer used in the testing device according to an embodiment of the present invention.

FIG. 8 depicts an orthogonal view of a computer 800 used in the testing device 100 according to an embodiment of the present invention. The computer 800 will be described in more detail in FIG. 9, but includes a PC board or Motherboard 810, along with a heat sink 820. In an exemplary embodiment, the computer 800 resides in the bottom of the testing device 100 and is physically separated from the sample carrier 120. The computer hosts the ports 320, 330, and 340 previously discussed.

Figure 9:
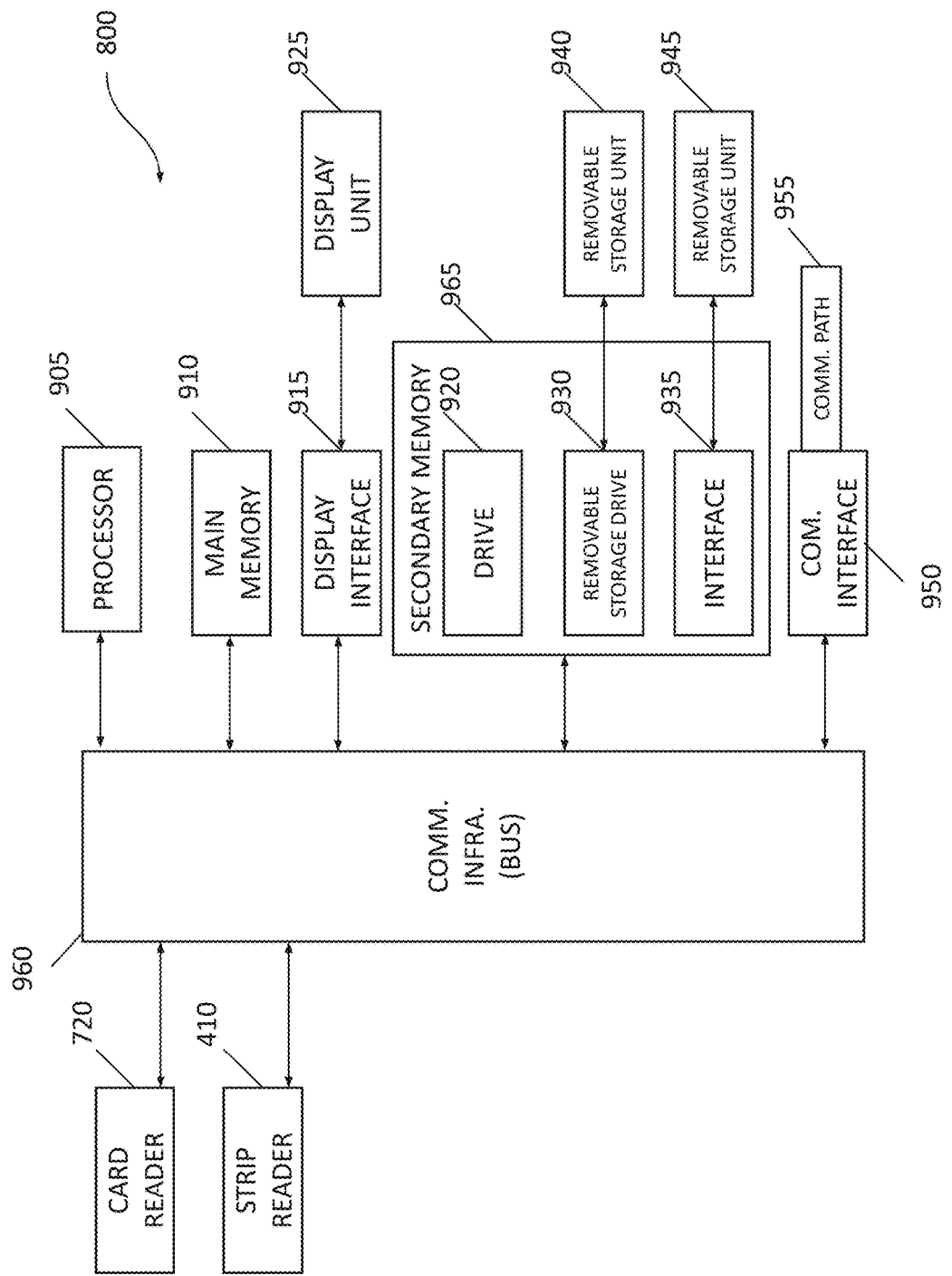
FIG. 9 depicts a block diagram of the computer used in the testing device according to an embodiment of the present invention.

FIG. 9 depicts a block diagram of the computer 800 used in the testing device according to an embodiment of the present invention. FIG. 9 depicts a high-level block diagram computer system 800, which can be used to implement one or more aspects of the present invention. More specifically, computer system 800 can be used to implement some hardware components of embodiments of the present invention. Although one exemplary computer system 800 is shown, those skilled in the art after reading this disclosure will understand that other implementations are also possible. Computer system 800 includes a communication path 955, which connects computer system 800 to additional systems (not depicted) and can include one or more wide area networks (WANs) and/or local area networks (LANs) such as the Internet, intranet(s), and/or wireless communication network(s). In one exemplary embodiment, communication path 955 includes wireless local area network communication, mobile or cellular wireless communication, and wired (such as Ethernet) communication. Computer system 800 and additional system are in communication via communication path 955, e.g., to communicate data between them. The computer system 800 may also contain an optional internal battery and battery charger that allows the unit to be charged. Alternatively an external battery with a power cord connected to the unit may be used, where the external battery unit features the same input connector as the computer system, and the external battery unit may then be installed in the field to provide robustness against power outages or to be used in the field where wall power is not available. An example of such as device is sown in FIG. 15

Computer system 800 includes one or more processors, such as processor 905. Processor 905 is connected to a communication infrastructure 960 (e.g., a communications bus, cross-over bar, or network). Computer system 900 can include a display interface 915 that forwards graphics, text, and other data from communication infrastructure 960 (or from a frame buffer not shown) for display on a display unit 925. In a headless device, such as testing device 100, no display unit is present 925, although one may be added by connecting to HDMI port 320. Computer system 900 also includes a main memory 910, preferably random access memory (RAM), and can also include a secondary memory 965. Secondary memory 965 can include, for example, a hard disk or solid-state drive 920 and/or a removable storage drive 930, representing, for example, a floppy disk drive, a magnetic tape drive, or an optical disk drive. Removable storage drive 930 reads from and/or writes to a removable storage unit 940 in a manner well known to those having ordinary skill in the art. Removable storage unit 940 represents, for example, a floppy disk, a compact disc, a magnetic tape, solid state, or an optical disk, etc. which is read by and written to by removable storage drive 930. As will be appreciated, removable storage unit 940 includes a computer readable medium having stored therein computer software and/or data.

In alternative embodiments, secondary memory 965 can include other similar means for allowing computer programs or other instructions to be loaded into the computer system. Such means can include, for example, a removable storage unit 945 and an interface 935. Examples of such means can include a program package and package interface (such as that found in video game devices), a removable memory chip (such as an EPROM, or PROM) and associated socket, and other removable storage units 945 and interfaces 935 which allow software and data to be transferred from the removable storage unit 945 to computer system 800.

Computer system 800 can also include a communications interface 950. Communications interface 950 allows software and data to be transferred between the computer system and external devices. Examples of communications interface 950 can include a mobile modem using, for example, 3G, 4G, and 5G networks, a network interface (such as an Ethernet card), a communications port, or a PCI, Mini PCI, or PCIe slot and card, for example. Software and data transferred via communications interface 950 are in the form of signals which can be, for example, electronic, electromagnetic, optical, or other signals capable of being received by communications interface 950. These signals are provided to communications interface 950 via communication path (i.e., channel) 935. Communication path 935 carries signals and can be implemented using wire or cable, fiber optics, a phone line, a cellular or mobile phone link, an RF link, and/or other communications channels.

In the present description, the terms "computer program medium," "computer usable medium," and "computer readable medium" are used to generally refer to media such as main memory 910 and secondary memory 965, removable storage drive 930, and a hard disk installed in hard disk drive 920. It may also refer to flash storage options, such as USB thumb drives or SD cards. Computer programs (also called computer control logic) are stored in main memory 910 and/or secondary memory 965. Computer programs can also be received via communications interface 390. Such computer programs, when run, enable the computer system to perform the features of the present invention as discussed herein. In particular, the computer programs, when run, enable processor 905 to perform the features of the computer system. Accordingly, such computer programs represent controllers of the computer system.

Computer System 960 also communicates with card reader 720 for reading identification or credit/debit card information from a user or patient and a strip reader 410 for optically reading the results on a test strip.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 10:
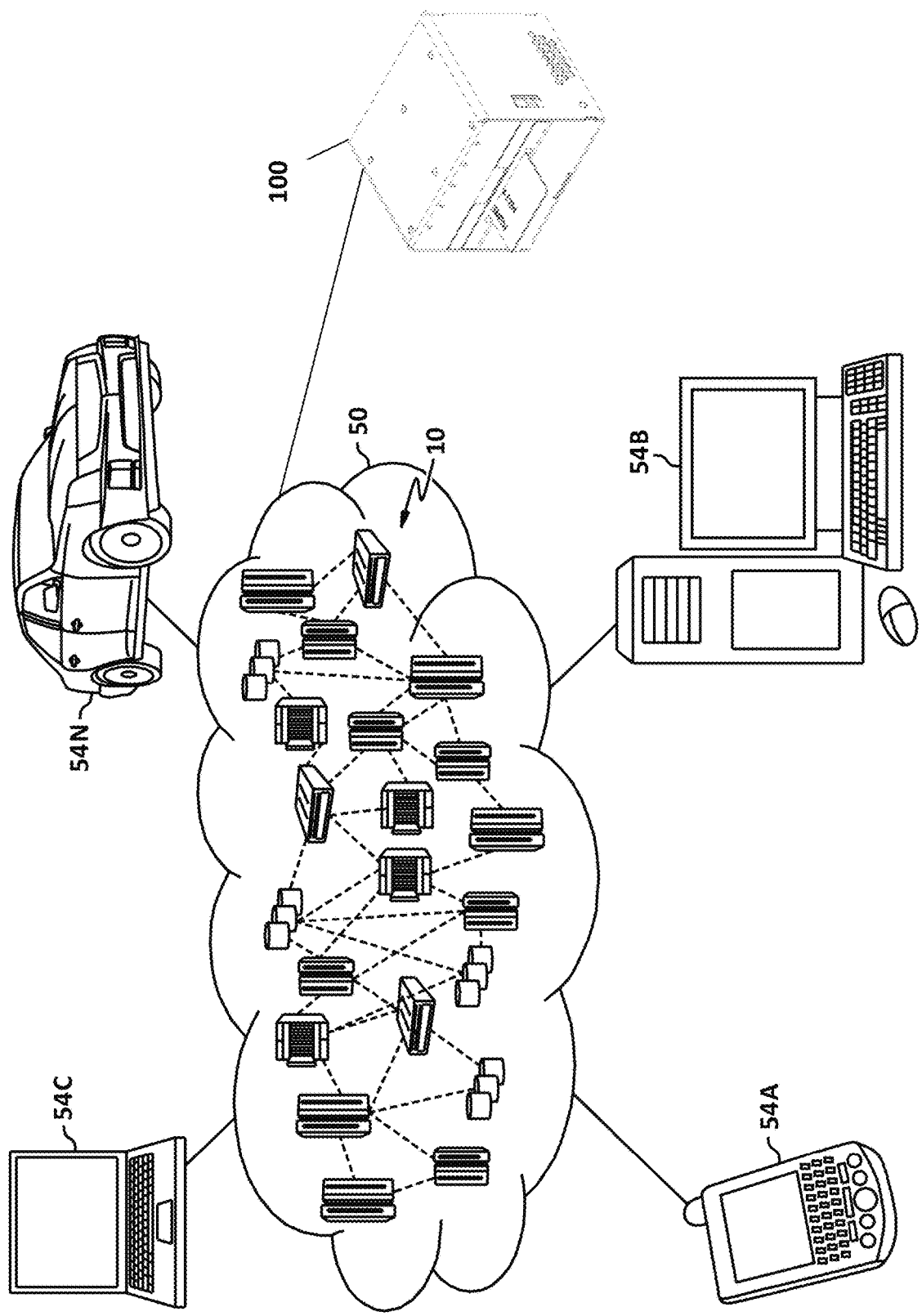
FIG. 10 depicts an environment for using a system in accordance with an embodiment of the present invention.

Referring now to FIG. 10, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, testing device 100 and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N and 100 shown in FIG. 1 are intended to be illustrative only and that computing nodes 10 and cloud computing environment 50 can communicate with any type of computerized device over any type of network and/or network addressable connection (e.g., using a web browser).

Figure 11:
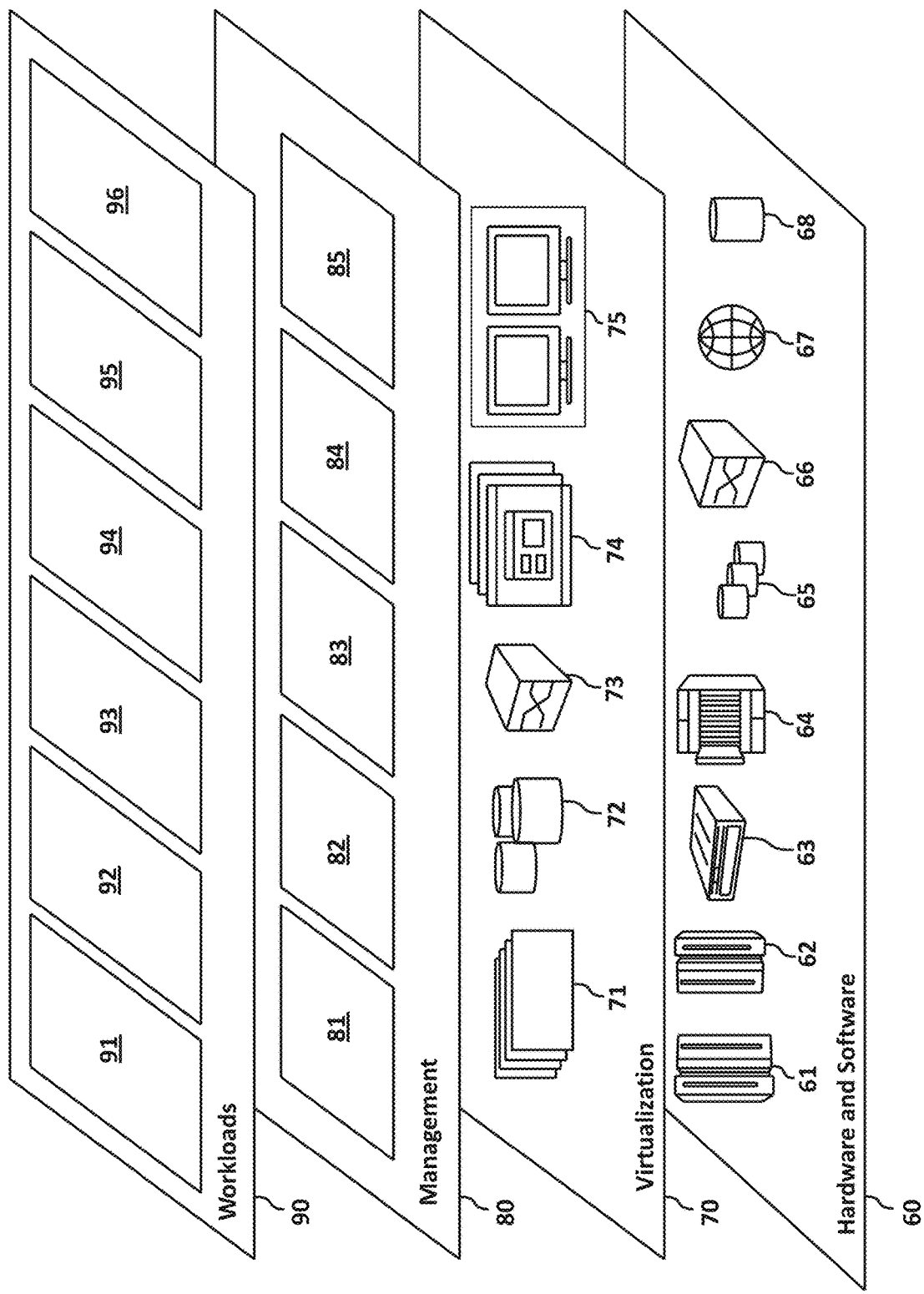
FIG. 11 depicts a high-level block diagram computer system, which can be used to implement one or more aspects of the present invention.

Referring now to FIG. 11, a set of functional abstraction layers provided by cloud computing environment 50 (FIG. 10) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65 storing test databases and results databases; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: data mining of test databases and results databases 91; software development and life-cycle management 92; machine learning of test strip analysis 93; headless testing device communications and control 94; computer (non-headless) communication and control 95; and testing analysis 96.

Figure 12A:
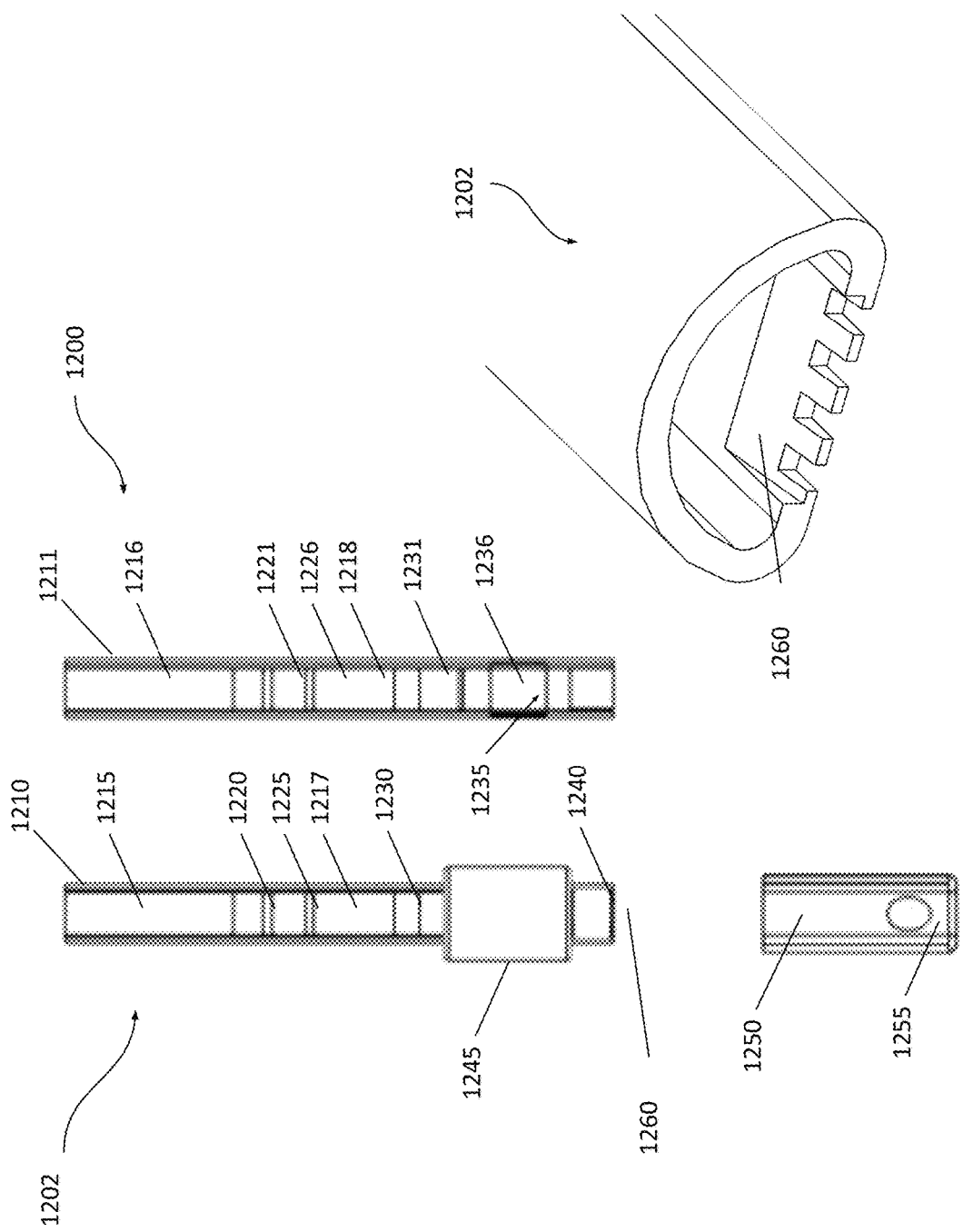
FIG. 12a depicts a top-down view of two assay tubes according to embodiments of the present invention.

FIG. 12 depicts a top-down view of two clear assays 1200 and 1202 according to an embodiment of the present invention. The clear assay 1202 includes a clear polyethylene ("PE") tube 1210 that is elongated and has a semicircular cross-section and contains an opening for an analyte. Materials other than PE can be used, such as polycarbonate, and those skilled in the art after reading this disclosure will appreciate that a wide range of other materials can be used in place of PE for the tube 1210. Other embodiments could have a rectangular or square cross-section and those skilled in the art will appreciate after reading this disclosure that any cross-sectional shape can be used that has a flattened portion. In an exemplary embodiment, the clear PE tube 1210 has an outer diameter of about 5.72 mm, an inner diameter of about 4.77 mm, and a height of about 3.90 mm. Inside the clear PE tube 1210 reside the following components (from top to bottom): printed symbology, such as a data matrix 1215, an LFA strip 1217 having one or more control lines 1220 and test lines 1225, a conjugate pad 1230, a sample pad 1240, and an absorbent material such as dental cotton may be placed in the bottom of the PE tube 1210.

A saliva inducing agent 1245, such as a candy, with or without vitamins, may be placed around the sample pad for stimulating saliva production in a patient. The candy need only be a thin layer to accomplish the goal of generating saliva from the patient, and the candy may have a roughened surface to draw saliva or mucus from the patient's tongue or oral mucosa. The purpose of the roughened surface is to collect epithelial cells from the tongue surface by scraping the clear assay across the dorsal, lateral, or ventral surfaces of the tongue. The decision on which areas are to be scraped is determined by the type of test. The patient places the candy or end of the PE tube 1210 in her mouth and the dental cotton draws up the saliva from the patient to the LFA strip 1217, while feature 1260 aids in scraping off cells from the areas touched by the tube.

The clear assay 1200 includes a clear PE tube 1211 that is elongated and has a semicircular cross-section and contains an opening 1235 for an analyte. Materials other than PE can be used, such as polycarbonate, and those skilled in the art after reading this disclosure will appreciate that a wide range of other materials can be used in place of PE for the tube 1210. Other embodiments could have a rectangular or square cross-section and those skilled in the art will appreciate after reading this disclosure that any cross-sectional shape can be used that has a flattened portion. In an exemplary embodiment, the clear PE tube 1211 has an outer diameter of about 5.72 mm, an inner diameter of about 4.77 mm, and a height of about 3.90 mm. Inside the clear PE tube 1211 reside the following components (from top to bottom): printed symbology, such as a data matrix 1216, an LFA strip 1218 having one or more control lines 1221 and test lines 1226, a conjugate pad 1231, and an analyte pad 1236. An analyte opening 1235 for receiving an analyte is placed in the PE tube 1210.

The clear assays described herein have a number of advantages over prior art cassettes. The clear assays can only stably be placed within a testing device in a single position, wherein other geometrical shapes, such as the rectangular prior art cassettes, can easily, and in fact are often easily, placed in testing devices upside down. This is due to the fact that the clear assays are rounded except on the flattened bottom side. Additional benefits are described in the following paragraph.

This method of collecting saliva is superior to methods that require unsanitary spitting into a tube or onto a strip, which for a child, for example, can be quite difficult. This invention is also substantially less polluting, and produces much less plastic and biologically hazardous waste compared to cassettes containing LFA strips. Because this solution eliminates the need for spit-cups or other forms of intermediary collection devices, the amount of waste generated is substantially less. Research indicates that virus production in the oral cavity is more prevalent in the epithelial cells of the tongue, since these cells have a high number of ACE2 receptors that the virus can bind to. Thus, a feature to collect cells from the lining of the tongue itself rather than the saliva itself is likely to increase sensitivity. Such a feature 1260 is shown including a ramp and teeth that will promote abrasive action and collection of cells as the tube is pushed across the tongue.

The data matrix 1215 uniquely identifies the sample, connecting it to the patient. In an exemplary embodiment of the invention, the barcode is a data matrix format based on ISO/IEC 16022:2006(E) and measures 8 mm long and 4 mm wide. A manufacturer code, supplier code, profile code (denoting disease being tested for), year code, day code, and serial number are encoded in the barcode 1215. When a patient is provided with the clear assay 1200, his information is entered into the central database along with a scan of the barcode, thus linking them together. This can be performed by the patient, for example, using her phone, or by a healthcare provider who is giving the clear assay 1200 to the patient.

Figure 13:
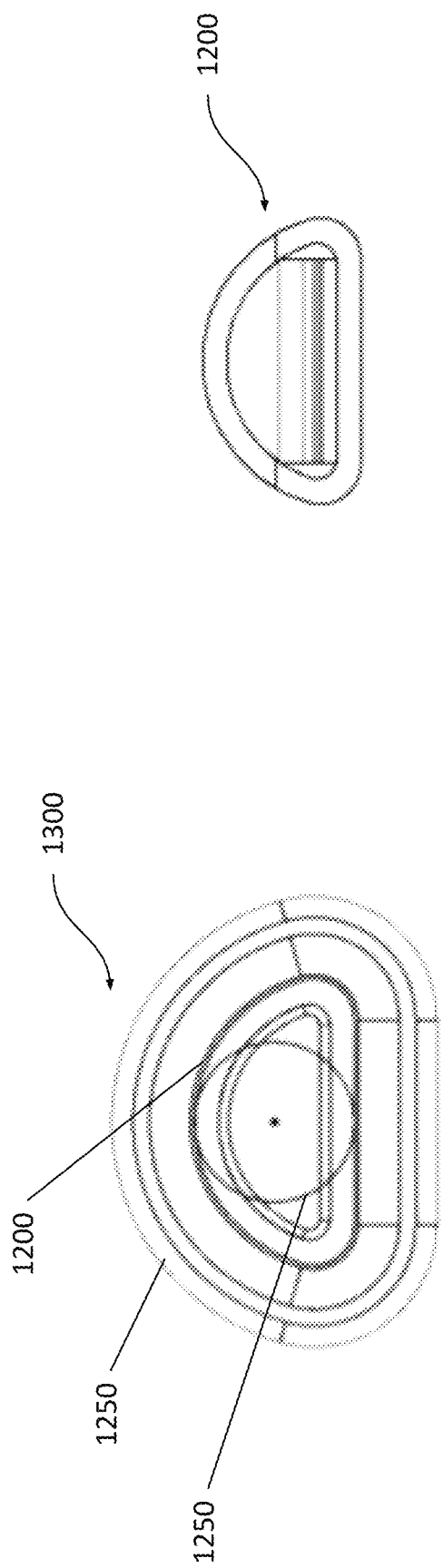
FIG. 13 depicts an end view of the assay tube according to an embodiment of the present invention.

A cap 1250 is also provided that includes a gelcap 1255 containing a liquid having one or more of sterile water, a lysis buffer solution, a detergent, a PH stabilizer, sodium chloride, and hydrochloric acid. A user places the open end of the clear assay 1200/1202 into the cap 1250 after he has provided his sample. The cap 1250 assists in keeping the system hygienic. FIG. 13 depicts an end view of the clear assay 1200 according to an embodiment of the present invention. When the cap is placed across the tube 1210/1211 and pressed on, the gelcap 1255 will burst and release the liquid within the inside of the tube 1210/1211, and cause the specimen collected in the cotton to be flooded with liquid, oversaturated, and the liquid will wash through the cotton and onto the analyte pad 1236 of the LFA strip 1217/1218.

FIG. 12*b* depicts a view of an assay tube used with an ampule according to embodiments of the present invention. In an alternative embodiment, an ampoule 1270 having a body 1272 and a cap 1271 may be used in lieu of the cap 1250 and gelcap 1255 combination, wherein the ampoule 1270 contains the liquid described with respect to the gelcap 1255. A user removes the top 1271 of the ampoule and then inserts the clear assay 1200/1202 into the body 1272 of the ampoule in order to flood the cotton with the liquid and through to the analyte pad 1236 of the LFA strip 1217/1218.

Figure 12C:
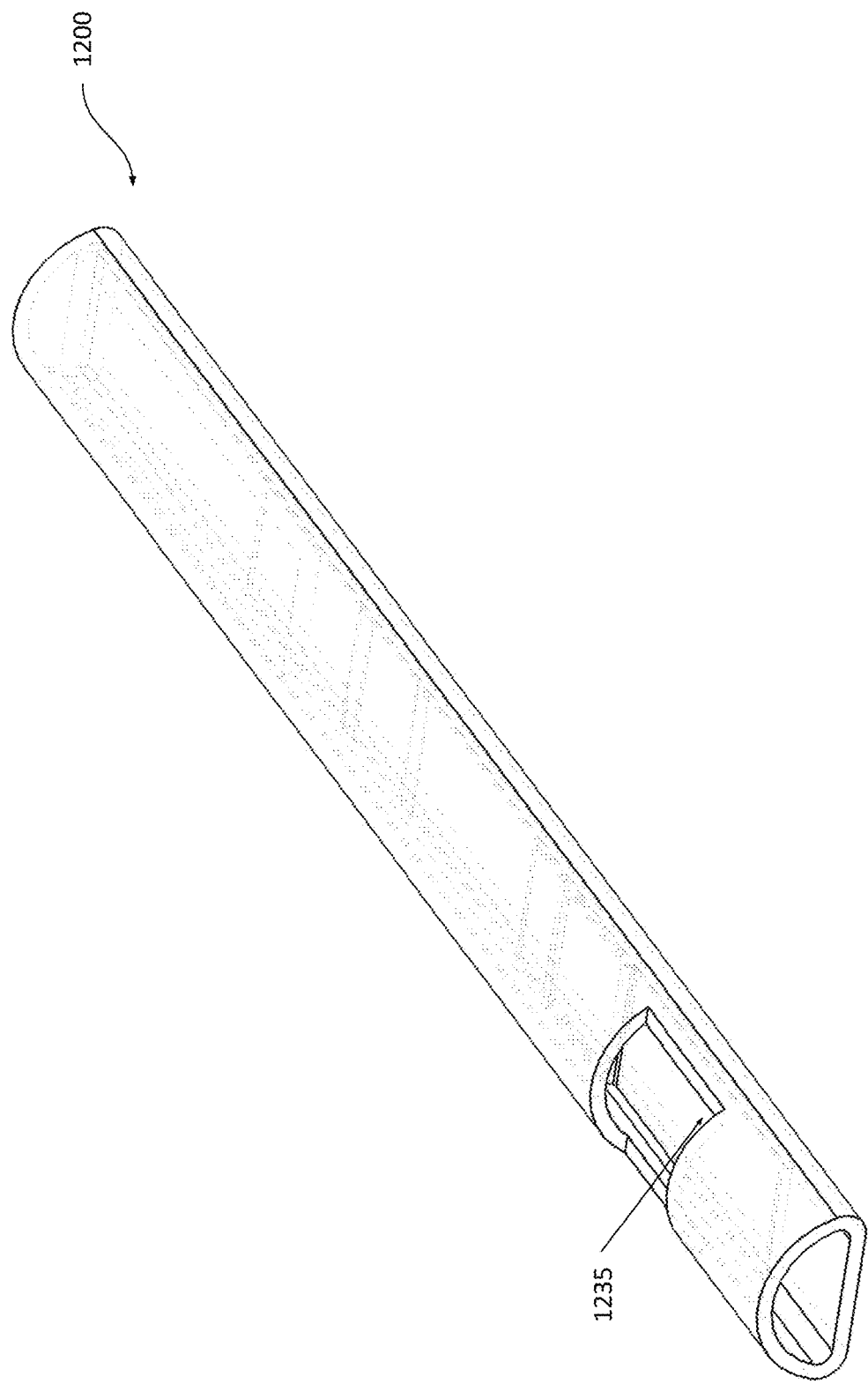
FIG. 12c depicts an orthogonal view of an assay tube according to embodiments of the present invention.

FIG. 12*c* depicts an orthogonal view to better display the opening 1235 of assay tube 1200 according to embodiments of the present invention.

Figure 14B:
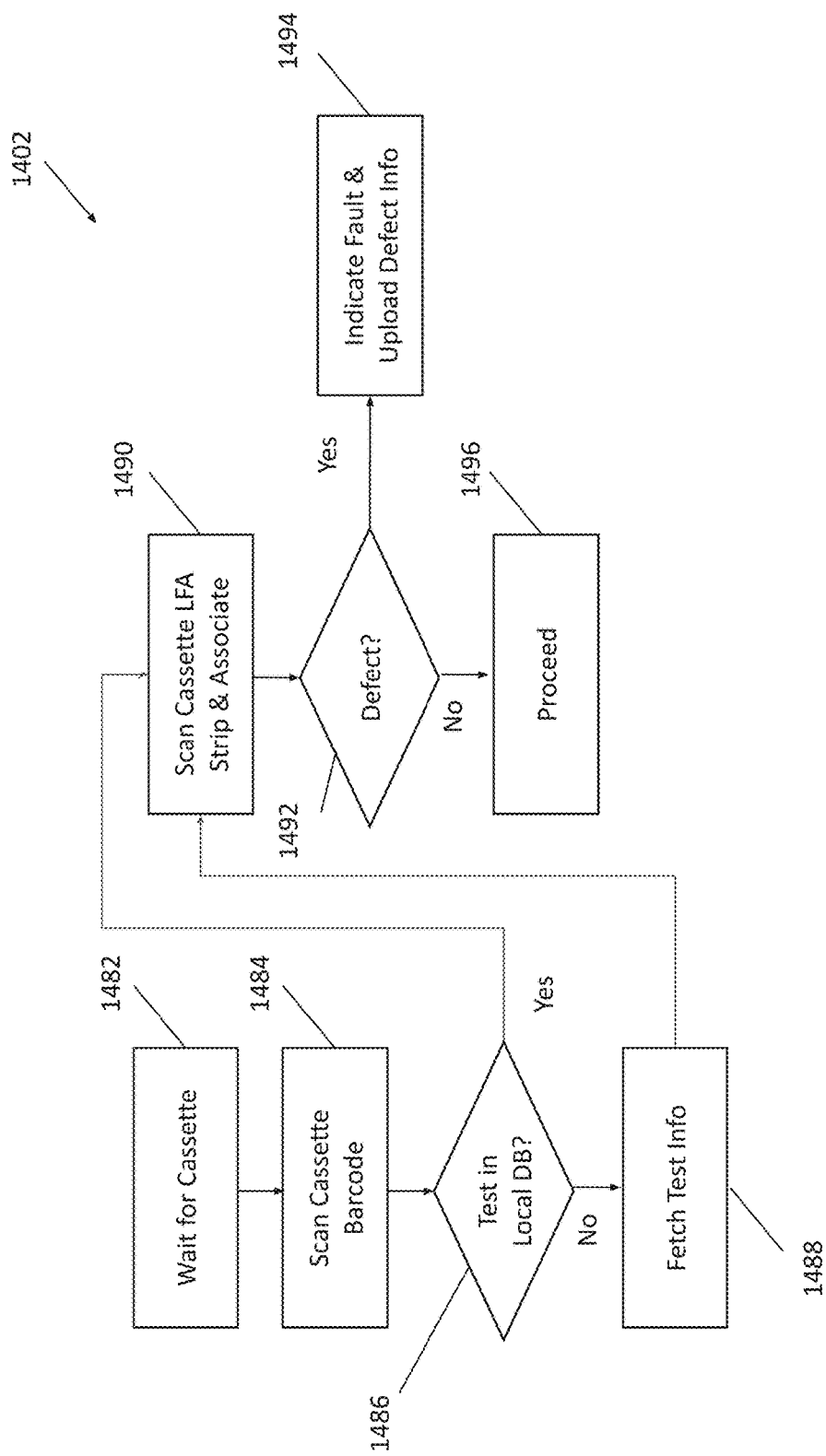
FIG. 14 depicts a flowchart for reading a test strip in an assay tube or sample carrier in accordance with an embodiment of the present invention.

FIG. 14*a* depicts a flowchart of a method 1400 for reading a test strip in a clear assay or sample carrier in accordance with an embodiment of the present invention. The method may perform an initial scan where an inserted cassette, clear assay or card is scanned for quality defects and association with a patient (block 1402). This block is explained in more detail in FIG. 14*b*. The method waits for the detection of a clear assay, cassette, or card (block 1405). The method uses a camera to detect visual features, such a visual feature may be the shape of the inserted cassette, text on the cassette, presence or absence of one or more barcodes, data matrices or QR codes, or one or more colors present on the cassette, for example. In an alternative embodiment, the method may use a mechanical switch to detect the presence of a clear assay, cassette, or card. If there is no clear assay, cassette, or card, the method waits in a loop that may be, for example, 1 second long, until the detection of the clear assay, cassette, or card.

The method scans a visual feature off of the clear assay, cassette, or card to identify a test that is being conducted and optionally a patient (block 1410). Any reference to cassette herein also incorporates the use of a clear assay. Embodiments of the invention may use a visual feature, such as text, a shape of the cassette, or identifiers of the cassette to determine the test being conducted. A visual feature may also be a barcode, QR code, or data matrix. For example, a COVID test may be being performed, but other tests as previously described, such as a seasonal flu test may be being performed. The method uses the visual feature to determine the test being conducted regardless of the alignment of the cassette with respect to the carrier. Alignment may include orientation of the cassette. In other words, regardless of orientation or alignment of the cassette, the visual feature is analyzed to determine the test being conducted.

In the case of a data matrix as the visual feature, information within the data matrix identifies a unique cassette identifier, a manufacturer code definition, supplier code definition, a profile code that together determine a test configuration profile to be used for this test. For other visual features, such as QR code, barcode, text, a shape of the cassette, identifiers of the cassette, or combinations thereof, in determining the test being conducted, the visual feature may initially be used to identify the test vendor. Once the test vendor is identified, if necessary, the specific test from that vendor is determined. Following identification of the vendor and specific test, the test configuration profile is determined.

A check is made to determine if the test configuration profile is present in a local database (block 1412). Test configuration profiles are stored locally in, for example, an XML file. Each XML file may contain multiple test configuration profiles. If the test configuration profile is not present in the local database, a fetch is made to pull a configuration file from a central test database for storage in the local database (block 1414). Thus, new tests that are used in the field will cause the local database to update itself with information from the remote database.

The LFA strip is scanned (block 1420). To scan the LFA strip, the configuration file corresponding to the profile number provides brightness settings for LEDs that provide light at various wavelengths that will shine upon the LFA strip. The LEDs are turned on to that appropriate brightness level, and after a delay to permit the LEDs to arrive at the proper brightness and a camera to stabilize to take an image at that brightness level, images are taken by the camera. The number of images taken is indicated by the configuration file associated with the configuration profile. The areas of the LFA strip indicated by the profile to contain control and testing lines are analyzed for color and intensity and results are averaged between several images taken to determine numerical values to be presented as results of the LFA strip scan.

If the scan of the LFA strip is bad for any reason, an invalid result is indicated (block 1440) and the result indicating a fault may be uploaded to a central database in association with the patient's unique ID (block 1470). If the scan of the LFA strip is good, the LFA scan is compared to a testing database to determine an LFA test result (block 1450). The actual value data of each test is stored and sent back to the central patient database so that a graph can be plotted for tests taken of a patient over time to see the magnitude of viral load or antibody concentration over time. Also, mathematical models may be used to develop data across large data sets of patients to see for example efficacy of a vaccine as a function of IgG/IgM concentration from samples taken over time across a cohort of patients. Patient information that identifies a specific person, such as a social security number or national ID number, may optionally not be stored in the central patient database, with only demographic data retained.

The numerical values from the LFA strip scan are used as input to an algorithm that uses concentration versus intensity data stored in the configuration profile to calculate a test result. The test result (which is an intensity) may be at or around the value of the intensity of the paper of the LFA strip which would indicate a negative test or a higher value to indicate there may be some concentration of reagent, antigen, or antibody present. When the test result, i.e., intensity, exceeds a threshold value stored in the configuration profile, a positive test result is returned. The following may be stored as a test result collection instance: one or more images of the actual LFA test strip used for the analysis; read values for the test and control lines; the test result, i.e., positive, negative, or invalid, according to the profile; the date, time, and GPS location of the test; serial number of the test from the bar code, QR code, or data matrix of the cassette or clear assay; serial number of the machine used for the test; operator code; and patient ID, drivers license number, ID number, health record numbers from a smart card reader or as read by the camera.

The test results, positive or negative, are provided to the patient via indicators on the testing device 100 (block 1460) and results as described above of the test may be uploaded to a central patient database in association with the patient's unique ID (block 1470). Regardless of test results, positive, negative, or invalid, the testing device is sanitized (block 1480). In addition, the method may account for privacy regulations or laws by periodically purging test information from the local database.

The barcode or datamatrix contains several digits that serve as an index into a configuration file, where the digits are interpreted as a profile code and provides the system information about the specific test that has been inserted into the machine. Based on this profile, the test device 100 configures the LED color; the combination of visual vs ultraviolet LEDs; where, what type of, and how many testing lines a test strip has; and which intensity of a testing line corresponds to the size of a viral load. This enables accurate qualitative reading of values rather than just positive or negative values based on a threshold. If the Profile Code read is not found in the configuration file, the system will reach out and fetch an updated configuration file from a known network location, thus enabling for new types of tests to be released into the market and into the test devices 100 installed in the field, updating based on demand rather than having to push an update to test devices 100 in the field, which may or may not be on or in use at any given time.

FIG. 14*b* depicts a flowchart of a method 1402 for performing an initial scan where an inserted cassette, clear assay or card is scanned for quality defects and association with a patient. The method waits for the detection of a clear assay, cassette, or card (block 1482). The method uses a camera to detect visual features, such a visual feature may be the shape of the inserted cassette, text on the cassette, presence or absence of one or more barcodes, data matrices or QR codes, or one or more colors present on the cassette, for example. In an alternative embodiment, the method may use a mechanical switch to detect the presence of a clear assay, cassette, or card. If there is no clear assay, cassette, or card, the method waits in a loop that may be, for example, 1 second long, until the detection of the clear assay, cassette, or card.

The method scans a visual feature off of the clear assay, cassette, or card to identify a test that is being conducted based on a visual feature and optionally a patient (block 1484). Identification of a vendor and specific test is made based on the visual feature. Following identification of the vendor and specific test, the test configuration profile is determined.

A check is made to determine if the test configuration profile is present in a local database (block 1486). Test configuration profiles are stored locally in, for example, an XML file. Each XML file may contain multiple test configuration profiles. If the test configuration profile is not present in the local database, a fetch is made to pull a configuration file from a central test database for storage in the local database (block 1488). Thus, new tests that are used in the field will cause the local database to update itself with information from the remote database.

The LFA strip is scanned (block 1490). To scan the LFA strip, the configuration file corresponding to the profile number provides brightness settings for LEDs that provide light at various wavelengths that will shine upon the LFA strip. The LEDs are turned on to that appropriate brightness level, and after a delay to permit the LEDs to arrive at the proper brightness and a camera to stabilize to take an image at that brightness level, images are taken by the camera. The number of images taken is indicated by the configuration file associated with the configuration profile. The areas of the LFA strip indicated by the profile to contain control and testing lines are analyzed for color and intensity and results are averaged between several images taken to determine numerical values to be presented as results of the LFA strip scan. At this point, the method will read a patient's identification card that is inserted or scanned by the testing device 100 and locally store patient information that is then associated with the unique cassette identifier.

A machine learning engine, described in a following paragraph, that is pushed from the central test database analyzes the one or more images of the LFA strip and carrier in order to look for quality defects in the LFA strip and the cassette containing the LFA strip, such as: discoloration of the LFA strip; misalignment of the LFA strip within the cassette; breaks in the LFA strip; dust; debris on the LFA strip; plastic defects; and, defects in the visual feature (block 1492). If a defect is found that could affect the quality of the test result from reading the LFA strip, an error is generated and the one or more images of the LFA strip and carrier are stored, along with environmental information, such as temperature and humidity, a time stamp, and the specific nature of the quality defect.

The error triggers an alarm to an operator of equipment implementing this method, with the alarm identifying that there is an error with the LFA strip and carrier by setting an LFA read bad flag (block 1494). Furthermore, the information gathered based on the visual feature scanned earlier in the method, the images of the LFA strip and carrier, environmental information, time stamp, and specific nature of the quality defect are uploaded to the central test database. At the central test database the information received may be stored by the test kit vendor and may be supplied to the test kit vendor in order to provide quality control feedback. If no defects are found, information gathered is uploaded to the central test database (block 1496).

Operation of the learning function of the machine learning engine will now be described. The machine learning engine resides at either the central test database or on the same or similar computing platform as is used to implement this method. A learning computer platform hosting the machine learning engine is fed a series of good (meaning quality defect free) carriers having good LFA strips within, with an operator instructing the machine learning engine that these are examples of good carriers and LFA strips. In addition, a series of carriers having categorized quality defects is also fed to the machine learning engine, enabling the machine learning engine to learn quality defects and develop the ability to categorize those quality defects. In an alternative embodiment, images of cassettes and LFA strips are categorized and fed into the machine learning engine in lieu of using actual cassettes and LFA strips and the machine learning engine learns from those categorized images. Similarly, images of good cassettes and LFA strips may be used to train the machine learning engine about good cassettes and LFA strips that have no quality defects.

If the scan of the LFA strip is bad for any reason, an invalid result is indicated (block 1440) and the result indicating a fault may be uploaded to a central database in association with the patient's unique ID (block 1470). If the scan of the LFA strip is good, the LFA scan is compared to a testing database to determine an LFA test result (block 1450). The actual value data of each test is stored and sent back to the central patient database so that a graph can be plotted for tests taken of a patient over time to see the magnitude of viral load or antibody concentration over time. Also, mathematical models may be used to develop data across large data sets of patients to see for example efficacy of a vaccine as a function of IgG/IgM concentration from samples taken over time across a cohort of patients. Patient information that identifies a specific person, such as a social security number or national ID number, may optionally not be stored in the central patient database, with only demographic data retained.

The numerical values from the LFA strip scan are used as input to an algorithm that uses concentration versus intensity data stored in the configuration profile to calculate a test result. The test result (which is an intensity) may be at or around the value of the intensity of the paper of the LFA strip which would indicate a negative test or a higher value to indicate there may be some concentration of reagent, antigen, or antibody present. When the test result, i.e., intensity, exceeds a threshold value stored in the configuration profile, a positive test result is returned. The following may be stored as a test result collection instance: one or more images of the actual LFA test strip used for the analysis; read values for the test and control lines; the test result, i.e., positive, negative, or invalid, according to the profile; the date, time, and GPS location of the test; serial number of the test from the bar code, QR code, or data matrix of the cassette or clear assay; serial number of the machine used for the test; operator code; and patient ID, drivers license number, ID number, health record numbers from a smart card reader or as read by the camera.

The test results, positive or negative, are provided to the patient via indicators on the testing device 100 (block 1460) and results as described above of the test may be uploaded to a central patient database in association with the patient's unique ID (block 1470). Regardless of test results, positive, negative, or invalid, the testing device is sanitized (block 1480). In addition, the method may account for privacy regulations or laws by periodically purging test information from the local database.

Figure 15:
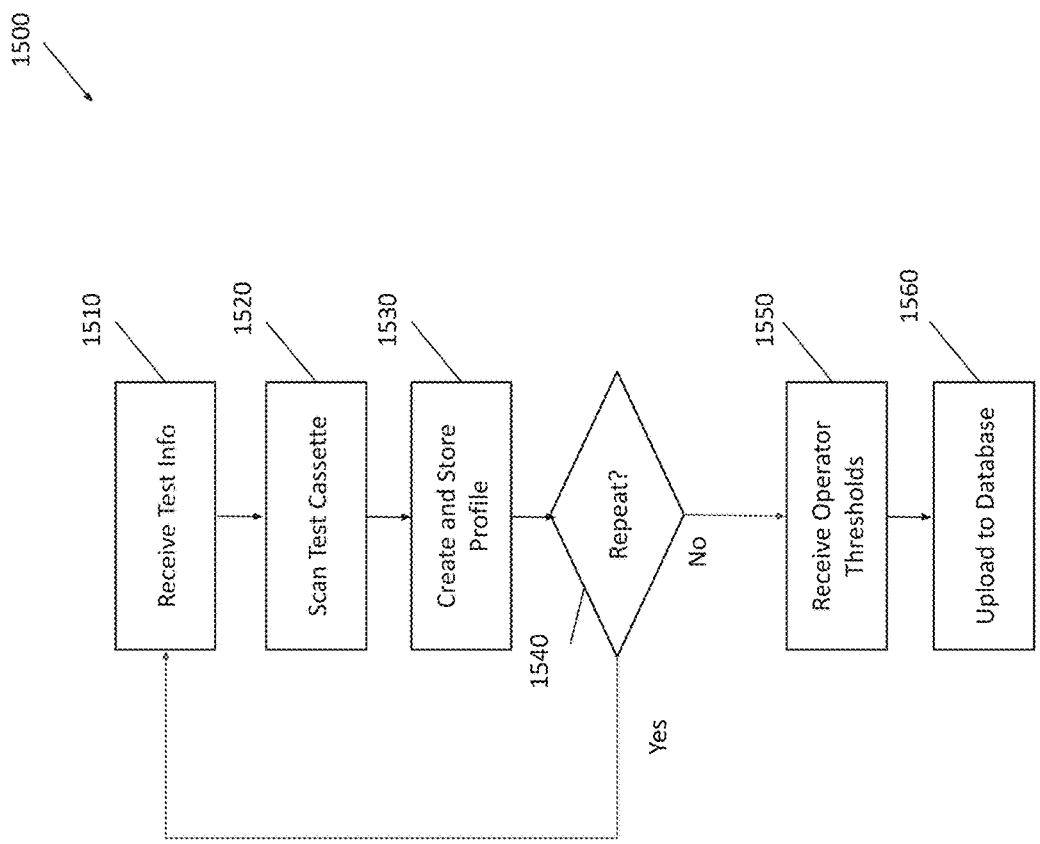
FIG. 15 depicts a flowchart for training a test strip reader in accordance with an embodiment of the present invention.

FIG. 15 depicts a flowchart 1500 for training a test strip reader in accordance with an embodiment of the present invention. Many different cassettes may be used in conjunction with testing device 100. For each cassette, it is desirable to not only be able to provide a positive or negative test result, but also to read the quality of a testing line on the LFA strip and learn what level of response and color of line for a test corresponds to a level of antigen or antibody response. Therefore, a training method builds a configuration profile for each type of cassette in conjunction with an operator. The operator prepares and uses known concentrations of specimens while taking an image of the cassette with that concentration while observing the image taken on a screen. First, test information is received (block 1510). Test information includes, for example, the vendor of the test, type of test, and a number of control lines and testing lines. The test cassette is scanned (block 1520) and an image taken of the cassette. A profile is created and stored based on the image and operator input (block 1530). The operator may adjust the light setting, such as a level of LED RGB light from, for example, 0% to 100%, for each color Red, Green, and Blue, as well as various ultraviolet light wavelengths from 200 nm up to 350 nm in increments of 10 nm, for example. All LEDs may not be needed for any particular test. An infrared LED may also be similarly used and adjusted.

When the operator determines that an acceptable LED collar and level combination for a given test has been determined, the configuration profile for that test is stored. The configuration profile that is stored includes, for example, test name, data, time, vendor, type of test, number and types of control lines and testing lines, LED values for the acceptable reading results, and an image of the test that produced the stored results.

The process may be repeated for additional cassettes with different concentrations but of the same type (block 1540), with those additional results saved in the configuration profile for that test. The operator determines what thresholds will be set for positive and negative tests, along with parameters that indicate and invalid test, such as a missing control line, missing bard code, or expired date of test, for example (block 1550). That information is also stored in the configuration file. When the operator is satisfied that the configuration file is complete, the configuration file is uploaded to a central test database (block 1560).

Figure 16:
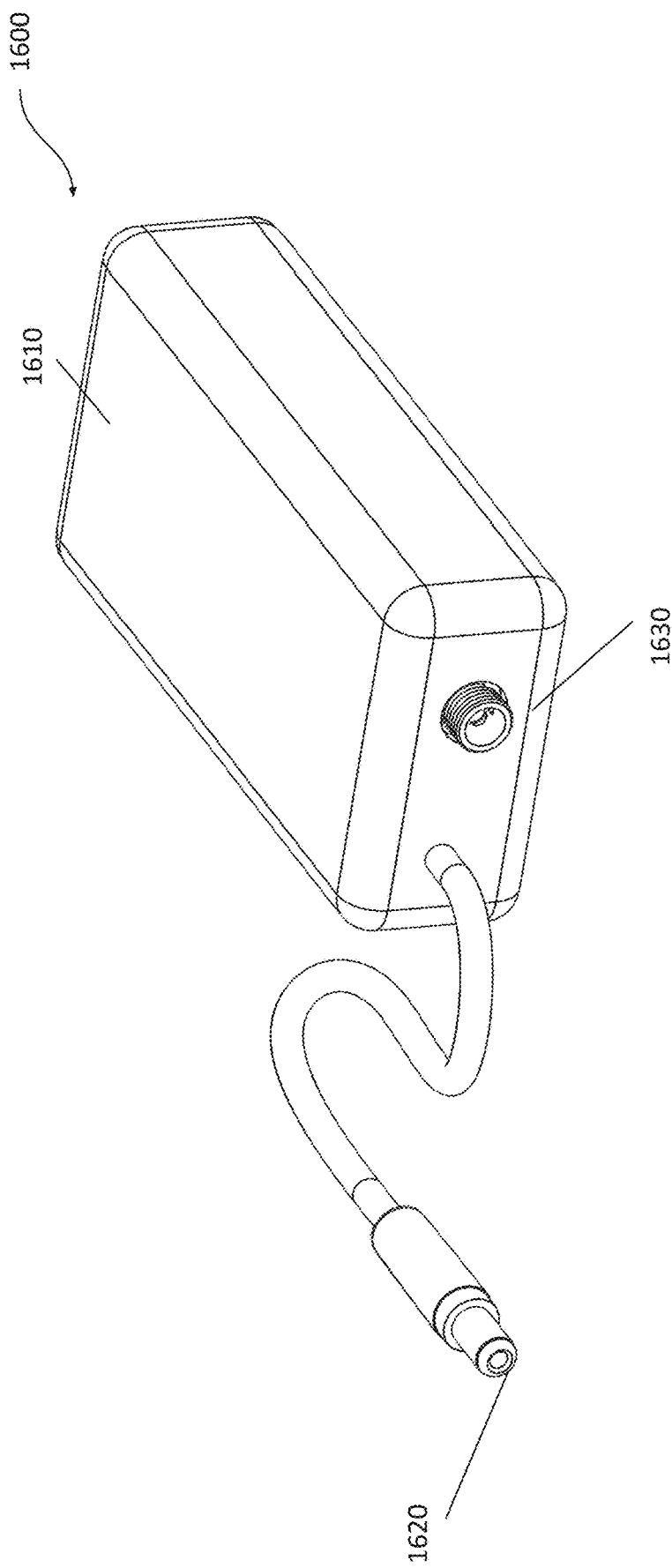
FIG. 16 depicts an orthogonal view of a battery pack for the testing device according to an embodiment of the present invention.

FIG. 16 depicts an orthogonal view of a battery pack 1600 for the testing device 100 according to an embodiment of the present invention. Battery pack includes an encased battery 1610 having a power input port 1630 for accepting a DC power supply and an output port 1620 for plugging in to a power input port of the testing device 100. By using battery pack 1600, testing device 100 may be used without needing an AC power source present.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A system, comprising:
   a processor;
   memory coupled to the processor;
   a communications interface coupled to the processor for communicating with a central test database;
   a carrier for receiving a cassette containing a lateral flow assay ("LFA") strip;
   an LFA strip reader coupled to the processor for taking an image of the LFA strip and cassette and transmitting the image to the processor, wherein the processor analyzes the image to determine a vendor of the cassette, analyzes the image of the LFA strip using a machine learning engine for quality defects in the LFA strip, generates an error when a quality defect is detected in the LFA strip, and reports the error to the central test database.

2. The system of claim 1, further comprising an environmental sensor for sensing environmental data, the environmental sensor in communication with the processor to send the environmental data to the processor.

3. The system of claim 2 wherein the environmental sensor is selected from a group consisting of a temperature sensor and a humidity sensor.

4. The system of claim 2, wherein reporting the error further comprises sending the environmental data to the central test database for storage.

5. The system of claim 1 wherein reporting the error comprises sending the image of the LFA strip and cassette along with an identity of the vendor to the central test database for storage.

6. The system of claim 1 wherein quality defect is one or more of a break in the LFA strip, dust, debris on the LFA strip, plastic defects, and defects in a visual feature on the carrier.

7. The system of claim 1, wherein the processor is further operable to download the machine learning engine over the communication interface.

8. The system of claim 1, further comprising a patient identification reader in communication with the processor, the patient identification reader operable to read patient identification information and provide the patient identification information to the processor and the processor further operable to associate the patient identification information with a unique cassette identifier determined from a visual feature on the carrier.

9. A method comprising:
   receiving a cassette containing a lateral flow assay ("LFA") strip at a carrier;
   taking an image of the LFA strip and cassette;
   transmitting the image to a processor;
   analyzing the image at the processor to determine a vendor of the cassette and to identify quality defects in the LFA strip, using a machine learning engine;
   generating an error when a quality defect is detected in the LFA strip; and
   reporting the error to a central test database, such that a result of the LFA strip with the quality defect is marked as invalid.

10. The method of claim 9, further comprising:
    sensing environmental data at an environmental sensor, sending the environmental data to the processor.

11. The method of claim 10 wherein the environmental sensor is selected from a group consisting of a temperature sensor and a humidity sensor.

12. The method of claim 10, wherein reporting the error further comprises sending the environmental data to the central test database for storage.

13. The method of claim 9, wherein reporting the error comprises sending the image of the LFA strip and cassette along with an identity of the vendor to the central test database for storage.

14. The method of claim 9, wherein quality defect is one or more of a break in the LFA strip, dust, debris on the LFA strip, plastic defects, and defects in a visual feature on the carrier.

15. The method of claim 9, further comprising:
downloading the machine learning engine by the processor to a local memory a communication interface.

16. The method of claim 9, further comprising:
reading patient identification information from the cassette, and providing the patient identification to the processor; and
associating the patient identification information with a unique cassette identifier determined from a visual feature on the carrier.

17. A system comprising:
a carrier for receiving a cassette containing a lateral flow assay ("LFA") strip;
an LFA strip reader coupled to a processor for taking an image of the LFA strip and cassette and transmitting the image to the processor; and
the processor to analyze the image of the LFA strip using a machine learning engine for quality defects in the LFA strip and generate an error when a quality defect is detected in the LFA strip and report the error to a central test database.

18. The system of claim 17, wherein quality defect is one or more of a break in the LFA strip, dust, debris on the LFA strip, plastic defects, and defects in a visual feature on the carrier.

19. The system of claim 17, wherein reporting the error comprises sending the image of the LFA strip and cassette along with an identity of a vendor to the central test database for storage.

20. The system of claim 17, further comprising:
an environmental sensor selected from a group consisting of a temperature sensor and a humidity sensor for sensing environmental data, the environmental sensor to send the environmental data to the processor; and
wherein reporting the error further comprises including the environmental data with the quality defect in the central test database.

* * * * *